US008900199B2

(12) United States Patent
Kawai et al.

(10) Patent No.: US 8,900,199 B2
(45) Date of Patent: Dec. 2, 2014

(54) NEEDLE TIP PROTECTOR AND INDWELLING NEEDLE ASSEMBLY

(75) Inventors: Katsunori Kawai, Ogaki (JP); Tatsuya Kudo, Takatsuki (JP); Hiroyuki Nakagami, Ritto (JP)

(73) Assignee: Nipro Corporation, Osaka (JP)

( * ) Notice: Subject to any disclaimer, the term of this patent is extended or adjusted under 35 U.S.C. 154(b) by 611 days.

(21) Appl. No.: 13/122,028

(22) PCT Filed: Oct. 1, 2009

(86) PCT No.: PCT/JP2009/005088
§ 371 (c)(1),
(2), (4) Date: Apr. 21, 2011

(87) PCT Pub. No.: WO2010/038471
PCT Pub. Date: Apr. 8, 2010

(65) Prior Publication Data
US 2011/0213307 A1    Sep. 1, 2011

(30) Foreign Application Priority Data

Oct. 3, 2008 (JP) ................................ 2008-259032
Oct. 3, 2008 (JP) ................................ 2008-259035
Oct. 3, 2008 (JP) ................................ 2008-259036

(51) Int. Cl.
*A61M 5/32* (2006.01)
*A61M 5/158* (2006.01)
*A61M 25/06* (2006.01)

(52) U.S. Cl.
CPC ............. *A61M 5/158* (2013.01); *A61M 5/3273* (2013.01); *A61M 25/0606* (2013.01); *A61M 25/0637* (2013.01); *A61M 2005/325* (2013.01); *A61M 25/0618* (2013.01)
USPC ...... 604/198; 604/110; 604/164.08; 604/192; 604/263

(58) Field of Classification Search
CPC . A61M 5/322; A61M 5/3202; A61M 5/3234; A61M 5/3213; A61M 5/3216; A61M 5/3243; A61M 5/3271; A61M 5/3273; A61M 25/0631
USPC ..................... 604/110, 164.08, 192, 198, 263
See application file for complete search history.

(56) References Cited

U.S. PATENT DOCUMENTS

| 5,300,045 A | 4/1994 | Plassche, Jr. |
| 5,458,658 A | 10/1995 | Sircom |

(Continued)

FOREIGN PATENT DOCUMENTS

| EP | 1 974 765 A1 | 10/2008 |
| JP | A-9-99073 | 4/1997 |

(Continued)

OTHER PUBLICATIONS

Oct. 18, 2012 Office Action issued in Japanese Patent Application No. 2008-259032 (with translation).

(Continued)

*Primary Examiner* — Scott Medway
(74) *Attorney, Agent, or Firm* — Oliff PLC

(57) ABSTRACT

A needle tip protector is configured in such a manner that a flexible plate is provided to a protector main body over which an action ring is mounted and that the flexible plate undergoes flexural deformation when the action ring is moved to a predetermined position relative to the protector main body. When the flexible plate undergoes flexural deformation, a needle tip of an inner needle to which the protector main body is mounted is protected by a protection part placed at a distal end of the flexible plate. The needle tip protector is also provided with a slip-stop mechanism for preventing the action ring from slipping out of the protector main body in an axial direction of the needle.

15 Claims, 21 Drawing Sheets

(56) References Cited

U.S. PATENT DOCUMENTS

| | | |
|---|---|---|
| 6,203,527 B1 | 3/2001 | Zadini et al. |
| 6,616,630 B1 | 9/2003 | Woehr et al. |
| 7,347,839 B2 | 3/2008 | Hiejima |
| 2003/0060771 A1 | 3/2003 | Bialecki et al. |
| 2008/0249478 A1 | 10/2008 | Ishikura et al. |

FOREIGN PATENT DOCUMENTS

| | | |
|---|---|---|
| JP | A-2001-514943 | 9/2001 |
| JP | A-2002-85558 | 3/2002 |
| JP | A-2002-248168 | 9/2002 |
| JP | A-2003-180833 | 7/2003 |
| JP | A-2004-242763 | 9/2004 |
| WO | WO 99/08742 A1 | 2/1999 |
| WO | WO 2005/079891 A1 | 9/2005 |
| WO | WO 2007/061144 A1 | 5/2007 |

OTHER PUBLICATIONS

Oct. 18, 2012 Office Action issued in Japanese Patent Application No. 2008-259035 (with translation).
International Preliminary Report on Patentability issued in International Application No. PCT/JP2009/005088 dated May 17, 2011.
International Search Report for International Patent Application No. PCT/JP2009/005088, mailed on Dec. 22, 2009.
Sep. 9, 2014 Extended European Search Report issued in European Patent Application No. 09817510.2-1662.

NEEDLE TIP PROTECTOR AND INDWELLING NEEDLE ASSEMBLY

TECHNICAL FIELD

The present invention relates to a needle tip protector used for protecting the needle tip and an indwelling needle assembly that is inserted into and left in the blood vessel during fluid transfusion or blood collection.

BACKGROUND ART

In the usual procedure of fluid transfusion or blood collection for the patient and others, a needle mounted to the distal end of a syringe, a needle mounted to the distal end of a tube connected to a container for fluid transfusion or blood collection, or an indwelling needle inserted through a hollow plastic needle and left in the patient's blood vessel and the like is used. Each of these needles has a sharp point. Therefore, they pose a risk of inadvertent pricking accidents where physicians, nurses, or disposal contractors might mistakenly prick their fingers with the needle tip. Once such an accident occurs, there is a risk of infectious diseases transmitted by the blood on the needle tip.

For this reason, needles with a protector that protects the needle tip without exposing it outside when being removed from the patient and others have recently started to become popular in order to prevent inadvertent pricking accidents from happening.

One of the examples of this needle tip protector is the one mounted to a needle comprising a protector main body with an insertion hole where the needle is inserted into and multiple elastic fingers placed so as to extend toward the needle tip, wherein the multiple elastic fingers are in the state of elastic deformation in one direction away from the needle, and the distal end of each elastic finger comes in contact with the outer surface of the needle inserted into the insertion hole of the protector main body in a slidable way (for example, see Patent Document 1 below). When such a needle provided with a protector is retracted from the patient and others, the needle moves relative to the protector while sliding over the distal end of the multiple elastic fingers. Such a movement of the needle allows each elastic finger to restore from the state of elastic deformation when the needle tip is placed in between the multiple elastic fingers. This allows the needle tip to be covered and protected by the multiple fingers.

Also, another kind of needle tip protector is known, comprising an elastic spring clip having, in an integrated manner, a supporting plate provided with an insertion hole where a needle is inserted into, and an extension plate stretching out from the supporting plate toward the needle tip and provided at the distal end with a protection part capable of covering the needle tip, wherein the extension plate is mounted to the needle while contacting the outer surface of the needle in a slidable way in the state of elastic deformation in a side direction away from the needle (for example, see Patent Documents 2 and 3 below). When this needle provided with a protector is retracted from the patient and others, the needle moves relative to the protector while sliding toward the extension plate. And, such a movement of the needle allows the extension plate to restore from the state of elastic deformation when the contact between the needle and extension plate is released. This allows the needle tip to be covered and protected with a protection part at the distal end of the extension plate.

Thus, in using a needle that can be fitted with a conventional needle tip protector, the needle tip can be protected without a special procedure for protection when being retracted from the patient and others.

However, each of these conventional needle tip protectors is mounted to a needle with its elastically deformed part contacting the outer surface of the needle. For this reason, it has been inevitable that the needle's sliding resistance against the protector is increased, thereby increasing the force needed to protect the needle tip when the needle provided with the protector is retracted from the patient and others while being moved relative to the protector. And, the larger the force to protect the needle tip, the more difficult it gets to perform the protection procedure by one hand, thereby posing a risk of making it hard to protect the needle tip right after retracting the inner needle or to surely move the needle relative to the protector to a location where the needle tip is protected.

BACKGROUND ART DOCUMENTS

Patent Documents

Patent Document 1: JP-A-9-99073
Patent Document 2: JP-A-2001-514943
Patent Document 3: JP-A-2002-248168

SUMMARY OF THE INVENTION

Problem the Invention Attempts to Solve

It is an object of the present invention to provide a needle tip protector having a construction that is improved to carry out the needle tip protection with lesser force surely and immediately after retraction of the needle from the patient and to make sure the needle tip protection can be maintained even more securely. It is also an object of the present invention to provide an indwelling needle assembly improved to protect the needle tip more securely by providing such needle tip protector.

Means for Solving the Problem

<1> A needle tip protector comprising: (a) a protector main body having an insertion passage where a needle is inserted, the protector main body being mounted against the needle by means of having the needle inserted into the insertion passage such that the protector main body being movable in an axial direction of the needle while extending along the same direction; (b) at least one flexible plate attached to the protector main body extending toward the needle tip at a location orthogonally away from the needle inserted into the insertion passage of the protector main body in a way that allows its distal end to undergo flexural deformation in a direction of getting closer to the needle; (c) a protection part placed at the distal end of the flexible plate that protects the needle tip by being placed at a protective position to cover the needle tip when the flexible plate undergoes flexural deformation in the direction of having its distal end get closer to the needle in a state where the protector main body is moved toward the needle tip of the needle inserted into the insertion passage; (d) an action ring that is externally fitted about the protector main body in a movable way in the axial direction of the needle and makes the protection part placed in the protective position by causing flexural deformation of the distal end of the flexible plate in the direction of having its distal end get closer to the needle through an advance movement toward a distal end side of the protector main body; and (e) a slip-stop mechanism that prevents the action ring from slipping out of the protector main body in the axial direction of the needle. The phrase "flexural deformation" used in this Specification refers to both types of flexural deformation, accompanied by and not accompanied by elastic deformation.

<2> The needle tip protector described in the mode <1> wherein the protector main body includes: a proximal end-side bottom plate having a first insertion hole as the insertion passage and arranged on a proximal end side of the protector main body so as to extend and cross the axial direction of the needle; a pair of flexible side plates as the flexible plate that are formed integrally with the proximal end-side bottom plate so as to extend from each of a pair of edges located on both sides of the first insertion hole of the proximal end-side bottom plate toward the needle tip of the needle inserted into the first insertion hole in a state of facing each other at a certain distance, and the distance between opposing surfaces gradually increases toward the needle tip to make the plates flexurally deformable in a direction of getting closer to each other; the protection part placed at the distal end of at least one of the pair of flexible side plates; a pair of parallel side plates facing each other in a direction orthogonal to the flexible side plates' opposing direction and extending parallel in the axial direction of the needle inserted into the first insertion hole; a distal end-side bottom plate having a second insertion hole as the insertion passage made at a location closer to the needle tip of the needle than that of the first insertion hole and integrally formed with a distal end edge of either of the pair of parallel side plates so as to extend toward another at the distal end side of the protector main body; and a housing part defined by a space enclosed by the distal end-side bottom plate, the proximal end-side bottom plate, the pair of flexible side plates and the pair of parallel side plates, and that houses a part of the needle inserted through the first insertion hole of the proximal end-side bottom plate and the second insertion hole of the distal end-side bottom plate; and a protruded engaging part integrally formed with the distal end-side bottom plate in a way that protrudes out of a surface of at least one of the pair of parallel side plates and the pair of flexible side plates, wherein as the action ring advances toward the distal end side of the protector main body, the protection part is placed at the protective position by having the pair of flexible side plates pushed inward with the action ring in the opposing direction of each other and flexurally deformed in the direction of getting closer to each other, and any slip-out of the action ring from the distal end side of the protector main body is prevented by means of engaging a front-end surface located on an advancing side of the action ring with the protruded engaging part of the distal end-side bottom plate.

<3> The needle tip protector described in the mode <2> wherein a bent part is provided at a midpoint in each extension direction of the pair of flexible side plates that bends a part closer to the distal end side than the midpoint in a direction away from the needle inserted in the first and second insertion holes, and distal end sides of the bent part of the pair of flexible side plates are made to be flexible pieces with the distance between the opposing surfaces gradually increasing toward the needle tip to make the plates flexurally deformable in the direction of getting closer to each other, whereas proximal end sides of the bent part of the pair of flexible side plates are made to be parallel extension parts that extend parallel to each other in the axial direction of the needle, and further, the pair of parallel extension parts are provided with a stopper mechanism that prevents flexural deformation in a direction of bringing the pair of flexible side plates closer to each other, and the pair of parallel side plates are integrally connected to the pair of parallel extension parts at each proximal end.

<4> The needle tip protector described in the mode <3> wherein a stopper plate is integrally formed with at least one of the pair of parallel extension parts extending toward at least another of the pair, and the stopper plate comprises the stopper mechanism and prevents the pair of parallel extension parts from flexurally deforming in the direction of getting closer to each other by means of having the stopper plate abut against the parallel extension part different from the one it is formed with.

<5> The needle tip protector described in any one of the modes <2> through <4> wherein the distal end-side bottom plate is arranged so as to extend and cross orthogonally to the axial direction of the needle inserted into the first and second insertion holes, and the protruded engaging part extends from an edge of the distal end-side bottom plate in a direction orthogonal to the axial direction of the needle.

<6> The needle tip protector described in any one of the modes <1> through <5> wherein the protection part is in a bent plate form having a first protection plate that extends from the distal end of the flexible plate toward the needle tip of the needle and a second protection plate that extends integrally from the distal end of the first protection plate closer to the needle tip in a direction opposite to the needle tip.

<7> The needle tip protector described in the mode <6> wherein the protection part is further provided with a pair of lateral lid plates facing each other in the direction orthogonal to the axial direction of the needle while placing the first and second protection plates of the protection part in between so as to cover each of lateral openings of the protection part in the bent plate form that open up to both sides in the direction orthogonal to the axial direction of the needle.

<8> The needle tip protector described in any one of the modes <1> through <7> wherein the protector main body is a single unit that is made of a metal plate.

<9> The needle tip protector described in any one of the modes <1> through <8> wherein the slip-stop mechanism includes: at least one anti-retraction tab provided on the protector main body in an elastically deformable way so as to extend toward the needle tip at a location orthogonally away from the axial direction of the needle inserted into the insertion passage of the protector main body, which allows the action ring to advance toward the distal end side of the protector main body by elastic deformation in the direction of getting closer to the needle, and when the protection part of the flexible plate is brought to the protective position by the action ring, prevents the action ring from moving back toward the proximal end side of the protector main body by means of restoring from the state of elastic deformation and contacting a rear-end surface of the action ring located on an opposite side of an advancing direction of the action ring; and at least one first engaging surface placed on the rear-end surface of the action ring that restricts elastic deformation of the anti-retraction tab in the direction of getting closer to the needle by engaging itself with the anti-retraction tab in contact with the rear-end surface.

<10> The needle tip protector described in the mode <9> wherein an insertion passage formation wall that forms the insertion passage is provided on the proximal end side of the protector main body so as to extend and cross the axial direction of the needle inserted into the insertion passage, whereas the at least one flexible plate comprises two flexible plates that are integrally formed with the insertion passage formation wall so as to extend toward the needle tip in the state of facing each other placing the needle inserted into the insertion passage in between, and further, the distance between the opposing surfaces of the two flexible plates is increased toward the needle tip, and as the action ring advances toward the needle tip, the two flexible plates are pressed in the direction of getting closer to the needle along an inner periphery of the action ring, thereby being flexurally deformed in the direction of getting closer to each other.

<11> The needle tip protector described in the mode <9> or <10> wherein insertion passage formation walls that form the insertion passage are each provided on the distal end and proximal end sides of the protector main body facing each other at a given distance in the axial direction of the needle inserted into the insertion passage, whereas through-holes are made through the two insertion passage formation walls, each being placed coaxially, and the insertion passage of the two insertion passage formation walls are each configured by these through-holes.

<12> The needle tip protector described in any one of the modes <9> through <11> wherein the at least one anti-retraction tab comprises two anti-retraction tabs that are provided on the protector main body so as to extend toward the needle tip in a state of being placed on both sides of the needle, whereas at least one first engaging surface comprises two first engaging surfaces that are each provided on the rear-end surface of the action ring being in contact with the two anti-retraction tabs.

<13> The needle tip protector described in any one of the modes <9> through <12> wherein the anti-retraction tab is integrally formed with the flexible plate by a cut-and-raise processing.

<14> The needle tip protector described in any one of the modes <9> through <13> wherein a second engaging surface is further provided on the rear-end surface of the action ring so as to restrict elastic deformation of the anti-retraction tab in the direction away from the needle by engaging itself with the anti-retraction tab in contact with the rear-end surface.

<15> The needle tip protector described in the mode <14> wherein a recessed groove is provided on the rear-surface of the action ring extending along a periphery of the action ring, and the first and second engaging surfaces are each configured on two side surfaces that extend along a periphery of the recessed groove.

<16> An indwelling needle assembly including an inner needle hub, an inner needle that extends out from a distal end of the inner needle hub, a hollow outer needle hub, and a hollow outer needle that extends out from a distal end of the outer needle hub, the inner and outer needle hubs being assembled with each other by having the distal end of the inner needle hub inserted into a proximal end-side opening of the outer needle hub under a state where the inner needle is inserted into the outer needle, characterized by that: the needle tip protector according to any one of claims 1-15 is mounted to the inner needle, a hemostasis valve is arranged to fit in a distal end side of the outer needle hub so as to prevent a blood flow into the outer needle hub from flowing out of the proximal end-side opening through an inner hole of the outer needle in a state where the inner needle is retracted from the outer needle, a cylindrical containing part that extends in an axial direction of the inner needle is provided on a distal end side of the inner needle hub at a distance from an outer periphery of the inner needle, whereas the protector main body mounted to the inner needle and the action ring externally fitted about the protector main body are arranged to fit in the cylindrical containing part, and the action ring is advanced relative to the protector main body as the inner needle and the protector main body move integrally when the inner needle is retracted from within the outer needle by integrally forming a latching protrusion with the action ring that extends out into the outer needle hub via a distal end-side opening of the cylindrical containing part and having the latching protrusion latched to the outer needle hub, and the protection part is placed at the protective position by flexurally deforming the flexible plate.

<17> The indwelling needle assembly described in the mode <16> wherein the latching protrusion of the action ring includes a circular reinforcing part that is provided in a middle portion of its extending direction and does not interfere with the protector main body and multiple extended latching pieces that are latched to the outer needle hub extending out from the circular reinforcing part into the outer needle hub.

<18> The indwelling needle assembly described in the mode <16> or <17> wherein an annular groove is formed along an inner peripheral surface of the outer needle hub extending continuously in its circumferential direction, and a projected latching rim that is formed protruding from a distal end of the latching protrusion thrusts into the annular groove to be latched.

<19> The indwelling needle assembly described in any one of the modes <16> through <18> wherein a protruded engaging part that releases an engagement of the latching protrusion with the outer needle hub is provided on the protector main body by means of engaging itself with the action ring and moving the action ring integrally with the protector main body when the inner needle and the protector main body move integrally further from a state where the protection part is placed at the protective position due to the flexural deformation of the flexible plate.

Effects of the Invention

In other words, the needle tip protector according to this invention, unlike conventional products, does not allow any of its part in the state of elastic deformation to contact the outer peripheral surface of the needle under the state of being mounted to the needle. Therefore, there will be no significant sliding resistance between the outer peripheral surface of the needle and the protector main body in contact with it when the needle and the protector main body mounted to it are relatively moved.

Therefore, the needle tip protector according to this invention allows protection of the needle tip with lesser force surely and immediately after retraction of the needle from the patient, and in addition, is able to make sure that such state of needle tip protection will be maintained even more securely.

Furthermore, the slip-stop mechanism prevents the action ring that places the protection part at the protective position from slipping out of the protector main body. This makes it possible to more securely maintain the state of needle tip protection with the protection part.

Also, the indwelling needle assembly according to this invention is provided with a needle tip protector having superior characteristics described above mounted on the inner needle retracted from the patient. Therefore, an indwelling operation of an outer needle in the patient can be carried out extremely safely and smoothly.

Especially in the protector according to the above mode <2>, a distal end-side bottom plate is integrally formed with one of the pair of parallel side plates, being provided with a protruded engaging part that prevents the action ring from slipping out of the distal end side of the protector main body by means of engaging itself with the action ring's front-end surface. Since the pair of parallel side plates extend parallel in the axial direction of the needle inserted into the first and second insertion holes of the protector main body, that is the extending direction of the protector main body, they are not subject to flexural deformation by the advance movement of the action ring, unlike the flexible side plate.

Therefore, a situation can be effectively avoided where the distal end-side bottom plate integrally formed with such parallel side plates and the protruded engaging part provided therein are displaced and the protrusion angle of the protruded engaging part relative to the central axis of the protector main body is modified as the action ring advances forward. This allows the protrusion angle of the protruded engaging part relative to the central axis of the protector main body to remain constant regardless of the flexural deformation and angle of the flexible side plate, unlike the case where the protruded engaging part is formed on the flexible side plate. As a result, the engagement of the protruded engaging part with the action ring's front-end surface can be securely maintained.

In addition, in case of the needle tip protector of this invention, the needle tip is housed in the housing part enclosed by those pair of flexible side plates, pair of parallel side plates, and distal end-side and proximal end-side bottom plates even when the needle tip is brought to a position between the pair of flexible side plates, for example, due to an inadvertent backward movement of the needle from the state of protection of the needle tip with the protection part. Because of this, an incident where the needle tip sticks out from within the protector main body can surely be prevented from occurring.

Also, especially in the needle tip protector according to the above mode <9>, the anti-retraction tab comes in contact with the action ring's rear-end surface when the action ring moves the protection part of the flexible plate to a protective position, preventing the action ring from retracting in the direction opposite to the needle tip. Also, it is configured in a way that elastic deformation of the anti-retraction tab in the direction of getting closer to the needle is prevented by having the anti-retraction tab get in contact and engaged with the first engaging surface placed on the action ring's rear-end surface.

Therefore, even when the flexible plate inadvertently undergoes flexural deformation in the direction of having its distal end closer to the needle, for some reason, a situation can be prevented favorably where the anti-retraction tab is elastically deformed in the direction of getting closer to the needle and the contact state of the anti-retraction tab with the action ring's rear-end surface is released. This allows the contact state of the anti-retraction tab with the action ring's rear-end surface to remain stable so that the action ring's position placed on the protector main body is securely maintained at the location where the protection part of the flexible plate is arranged in place at the protective position.

EMBODIMENTS FOR CARRYING OUT THE INVENTION

Figure 1:
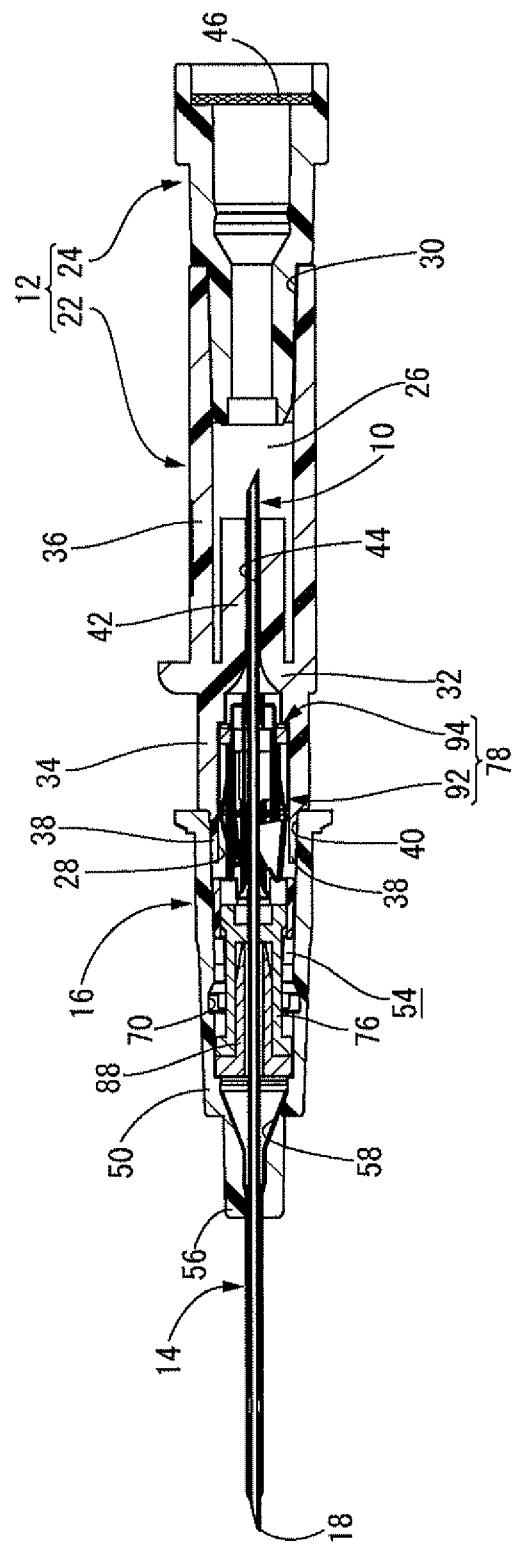
FIG. 1 is a longitudinal section diagram showing an embodiment of an indwelling needle assembly having a structure according to this invention.
Figure 2:
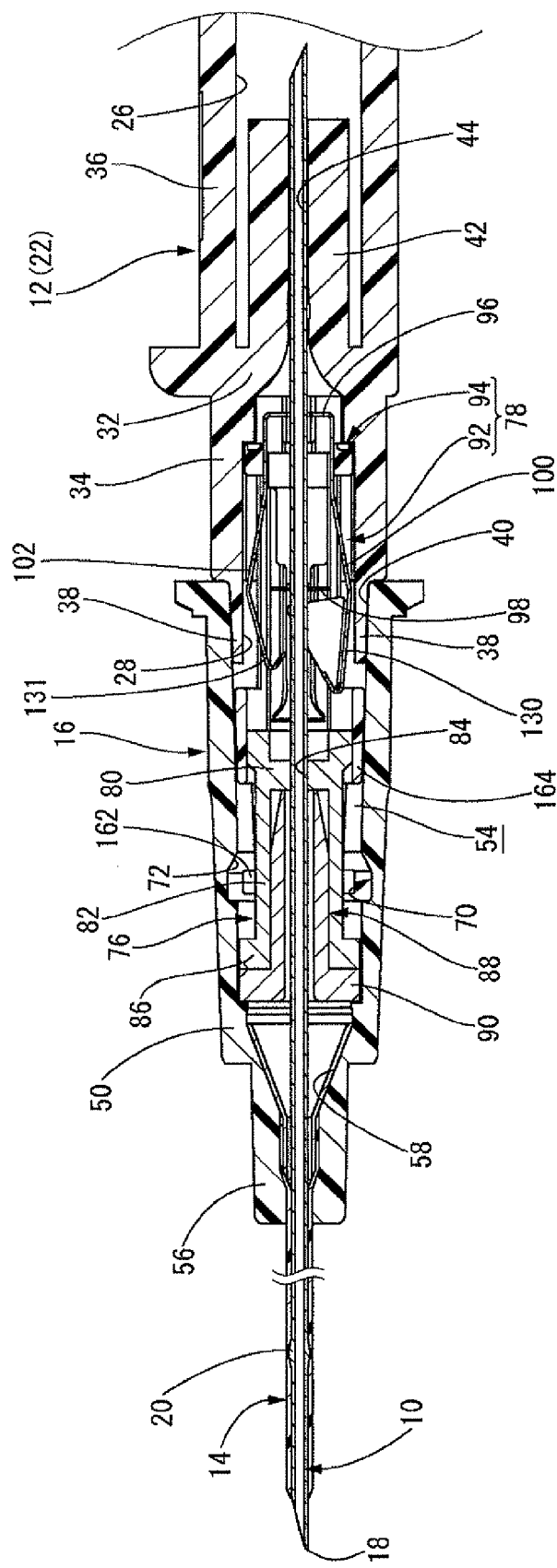
FIG. 2 is an enlarged view of essential parts of FIG. 1.

First of all, an embodiment of an indwelling needle assembly provided with a needle tip protector having a structure according to this invention is shown in FIG. 1 in its longitudinal section view, and a part thereof is shown in an enlarged view in FIG. 2. The indwelling needle assembly of the present embodiment comprises an inner needle 10, an inner needle hub 12 that fastens the proximal end (the right ends in FIGS. 1 and 2) of said inner needle 10, an outer needle 14 that is externally fitted about said inner needle 10, and an outer needle hub 16 that fastens the proximal end (the right ends in FIGS. 1 and 2) of said outer needle 14. In this Specification, the phrase "distal end side" refers to the distal side of the operator who performs a needle insertion procedure for the patient using an indwelling needle assembly or a needle tip protector, and the word "distal end" refers to the end part of the indwelling needle assembly or needle tip protector located on such distal side or that of each component comprising them, whereas the phrase "proximal end side" refers to the proximal side of the operator and the word "proximal end" refers to the end part of such proximal side.

Figure 3:
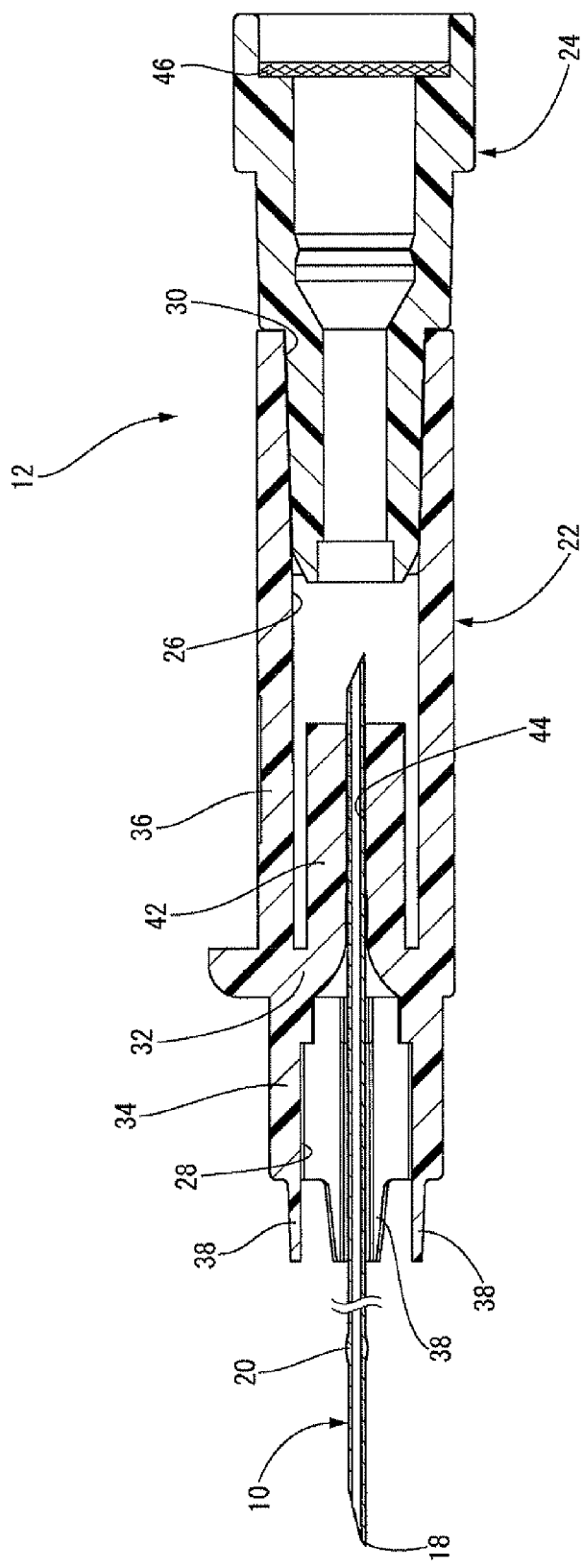
FIG. 3 is a longitudinal section diagram showing an inner needle and an inner needle hub possessed by the indwelling needle assembly shown in FIG. 1.

More specifically, as shown in FIG. 3, the inner needle 10 has a given length and is made of a hollow needle with a sharp point called a needle tip 18. Near the needle tip 18 of the inner needle 10, an engaging part 20 is formed. The engaging part 20 is formed in such a way that the tube walls near the needle tip 18 of the inner needle 10 are swollen out partially or entirely along its circumferential direction so that the diameter of such tube walls is made larger than other parts thereof. Meanwhile, the material forming the inner needle 10 is not limited to particular one, but metal materials such as stainless steel, aluminum, aluminum alloys, titanium, and titanium alloys, for example, are used as appropriate.

The inner needle hub 12 comprises a hub main body 22 and a cap 24. The hub main body 22, as a whole, is in an approximate cylindrical form wherein an inner hole 26 connects a distal end-side opening 28 to a proximal end-side opening 30 to open up outward. At the middle portion in the axial direction within the hub main body 22, a division wall 32 that divides the inner hole 26 into two sections in the axial direction is integrally formed. And, the distal end side of the forming portion of the division wall 32 of the hub main body 22 is made to be a cylindrical containing part 34 that connects to outside via the distal end-side opening 28, whereas the proximal end side of the division wall 32 is made to be a mounting cylinder 36 that connects to the outside via the proximal end-side opening 30.

The cylindrical containing part 34 is in an approximate cylindrical form that is located away on the outer circumferential side of the inner needle 10 extending in the axial direction thereof. Along the inner periphery of the end surface of the cylindrical containing part 34, a multitude (four in this case) of protruded plates 38 in a thin flat form extending in the axial direction are integrally provided at a given distance from each other in the circumferential direction. These multitude of protruded plates 38 are made to undergo flexural deformation toward inside of the cylindrical containing part 34. This allows the inner needle hub 12 to be inserted into a proximal end-side opening 40 of the outer needle hub 16 at the distal end of the cylindrical containing part 34 where the multitude of protruded plates 38 are formed (see FIG. 2).

On the other hand, within the mounting cylinder 36, a fixed cylindrical part 42 is integrally provided to the proximal end-side lateral surface of the division wall 32 so as to extend along the same axis as the mounting cylinder 36. Then, the inner needle 10 extending through the division wall 32 is fixed to an inner hole 44 of the fixed cylindrical part 42 being inserted, with its proximal end thrust in place, into the inner hole of the mounting cylinder 36. This allows the inner hole of the mounting cylinder 36 to connect into the inner hole (pore) of the inner needle 10.

The cap 24, as a whole, is in an approximate stepped cylindrical form with its distal end side portion having a smaller diameter than the proximal end side portion, whereas a ventilation filter 46 is installed at the proximal end-side opening. This ventilation filter 46 is characterized by transmitting air but not liquid. Such ventilation filter 46 includes, for example, sintered porous materials made by sintering polymeric materials such as polyethylene and materials containing hydrophilic, water soluble, or water swellable polymers as well as filter components made of hydrophobic non-woven fabrics and porous materials and the like.

Then, said cap 24 is assembled to the hub main body 22 in a detachable way by being pressed into the proximal end-side opening 30 of the hub main body 22 at the distal end of the smaller diameter on the opposite side of the mounted ventilation filter 46. This makes the inner needle hub 12 to be configured as a component to be assembled with the hub main body 22 and the cap 24.

Figure 4:
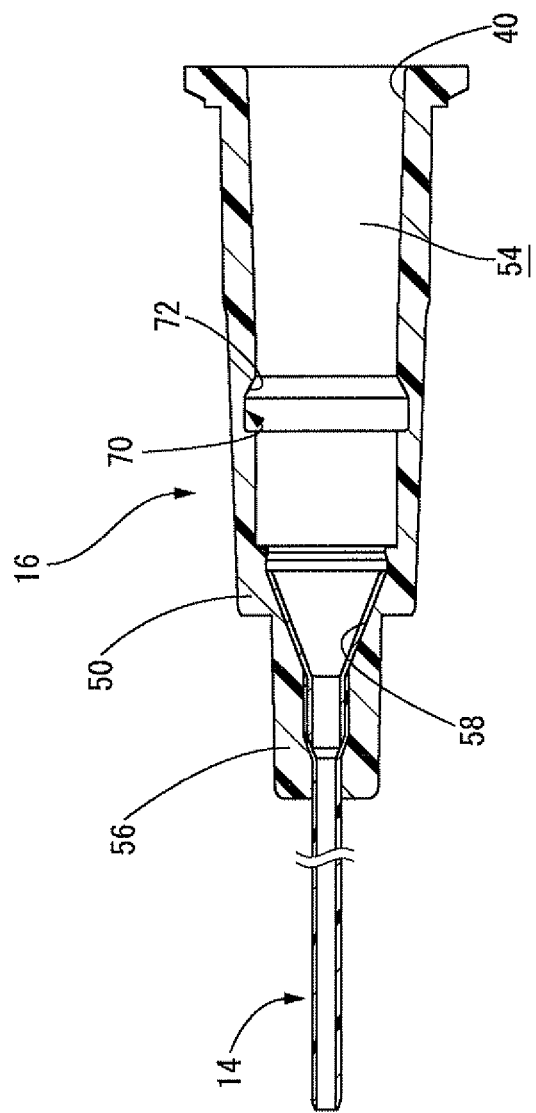
FIG. 4 is a longitudinal section diagram showing an outer needle and an outer needle hub possessed by the indwelling needle assembly shown in FIG. 1.

On the other hand, the outer needle 14 is made of a hollow tubule that is shorter than the inner needle 10 and externally fittable thereon, as shown in FIGS. 2 and 4. Unlike the inner needle 10, this outer needle 14 does not have a sharp point but its distal end surface is made to be a tapered surface that gradually reduces its diameter toward the distal end side. This keeps the resistance during the insertion of the outer needle 14, together with the inner needle 10, into the blood vessel of the patient as small as possible. Near the distal end of the outer needle 14, one or more pores may be made for the efficiency of in- and out-flows of liquid flowing inside.

Although the material of the outer needle 14 is not limited to particular one, it is desirable to have proper flexibility in order to avoid damaging blood vessel walls of the patient and others when it is left therein. From this point of view, as the material that forms the outer needle 14, ethylene-tetrafluoro-ethylene copolymer and various soft resins such as polyurethane, polyether nylon and polypropylene are preferably used. The outer needle 14 should preferably have transparency in order to allow monitoring of the liquid flow through the inside after it is left in the patient's blood vessel. Also the outer needle 14 may be combined with an X-ray contrast agent such as barium sulfate and barium carbonate in its composition so that its indwelling location can be tracked.

As evident from FIGS. 2 and 4, the outer needle hub 16 has an overall form of an approximate cylinder, whereas the inner hole is made in a hollow form that opens up outward via the proximal end-side opening 40. A containing part 54 is configured by the inner hole of this outer needle hub 16. On the distal end surface of the outer needle hub 16, a fixing protrusion 56 in a columnar shape is integrally formed on the same axis. A through-hole 58 is made at a distal end portion 50 of the outer needle hub 16 of the fixing protrusion 56 extending in the axial direction through them.

In the middle portion in the axial direction along the inner peripheral surface of the outer needle hub 16, an annular groove 70 is formed extending continuously in its circumferential direction all the way around. This annular groove 70 is made to be a tapered latch surface 72 in a tapered form wherein the side surface located on the proximal end side of the outer needle hub 16 reduces its diameter toward the proximal end.

Moreover, as shown in FIGS. 1 and 2, the inner needle 10 is inserted into the containing part 54 of the outer needle hub 16 via the proximal end-side opening 40 of the outer needle hub 16, and further inserted into the outer needle 14 that extends out from the distal end of the outer needle hub 16 communicating through said containing part 54. The inner needle hub 12 fixed at the proximal end of such inner needle 10 is also inserted into the proximal end-side opening 40 of the outer needle hub 16, that is, the proximal end side of the containing part 54 of the outer needle hub 16. This insertion of the inner needle hub 12 into the proximal end-side opening 40 of the outer needle hub 16 is, as mentioned above, realized by having the multitude of protruded plates 38 thrust into the proximal end-side opening 40 of the outer needle hub 16. In that way, the inner needle hub 12 and outer needle hub 16 are assembled to each other in an easily detachable manner.

Then, in the indwelling needle assembly of the present embodiment, a hemostasis valve 76 is contained in place on the distal end-side from where the inner needle hub 12 is inserted in the containing part 54 of the outer needle hub 16 under the state where the inner needle hub 12 and outer needle hub 16 are assembled to each other in the way mentioned above. Also, a needle tip protector 78 is contained in place in the cylindrical containing part 34 of the inner needle hub 12 under the state of being mounted to the inner needle 10.

More specifically, the hemostasis valve 76 comprises a similar structure to the one disclosed in, for example, Japanese Published Unexamined Application (Kokai) No. 2004-242763. In other words, the hemostasis valve 76 is made of a single component integrally formed using elastic body materials such as various rubber materials and thermoplastic elastomers and comprises an open-close part 80 and a cylindrical part 82. The open-close part 80 is in an approximate form of a thick disc having a smaller required outer diameter than the containing part 54 of the outer needle hub 16. In the center of this open-close part 80, a cut 84 is made to be pushed open by the inner needle 10. The cylindrical part 82 is in an approximate form of a thin cylinder and extends out integrally on the same axis from one side surface in the thickness direction of the open-close part 80 in a disc form. At the distal end of this cylindrical part 82, an outer flange 86 is integrally placed along the periphery in a form of an annular disc with a slightly larger outer diameter than the inner diameter of the containing part 54.

A pusher 88 is assembled to the hemostasis valve 76. This pusher 88 is made of hard resin materials and the like, and as a whole, is made in a form of a cylinder that is insertable into the inner hole of the cylindrical part 82 of the hemostasis valve 76. The outer peripheral surface of one end of this pusher 88 in the axial direction is made in a tapered form having a diameter getting smaller toward the one end in the axial direction. Also, at the other end of the pusher 88 in the axial direction, an outer flange 90 in a form of an annular disc is integrally placed along the circumference.

Then, the pusher 88 is coaxially inserted into the inner hole of the cylindrical part 82 of the hemo stasis valve 76. Under these conditions, the one end surface of the pusher 88 with its tapered outer peripheral surface is made in contact with the open-close part 80 of the hemostasis valve 76, whereas the outer flange 90 of the pusher 88 is made to overlap with the outer flange 86 of the hemostasis valve 76 and is assembled thereto.

An assembly of such hemostasis valve 76 and pusher 88 is inserted into and contained in place at the distal end side of the containing part 54 under the state where the outer surface of the outer flange 86 of the hemostasis valve 76 is pressed against the inner peripheral surface of the containing part 54 of the outer needle hub 16 and the outer flange 86 of the pusher 88 is made to butt against the inner surface of the distal end portion 50 of the outer needle hub 16. Under such a state of containment, the hemostasis valve 76 is prevented from moving easily in the axial direction within the containing part 54 by the frictional resistance based on restoring force of the outer flange 86 that is pressed against the inner peripheral surface of the containing part 54. The pusher 88 is also prevented from moving in the axial direction within the containing part 54 with the outer flange 90 sandwiched between the distal end portion 50 of the outer needle hub 16 and the outer flange 86 of the hemostasis valve 76. Or, an engaging part is provided along the inner circumference of the outer needle hub 16 where the hemostasis valve 76 and pusher 88 are engaged to, thereby restricting the movements of the hemostasis valve 76 and pusher 88. Then, the inner needle 10 inserted into the containing part 54 elastically deforms the open-close part 80 so as to push open the cut 84 of the hemostasis valve 76, and while being inserted through the cut 84, is inserted through the inner hole of the pusher 88 in the cylindrical part 82 of the hemostasis valve 76 as well as the through-hole 58 at the distal end portion 50 of the outer needle hub 16, and is further inserted through the outer needle 14.

When the inner needle 10 inserted this way through the outer needle 14 via the cut 84 of the open-close part 80 of the hemostasis valve 76 and each inner hole of the cylindrical part 82 and the pusher 88 is removed from the outer needle 14, as described later, the cut 84 of the hemostasis valve 76 is closed due to restoring force of the open-close part 80 from the state of elastic deformation. At that time, the gap between the inner peripheral surface of the containing part 54 of the outer needle hub 16 and the outer peripheral surface of the hemostasis valve 76 is sealed liquid-tight with the outer flange 86 of the hemostasis valve 76 pressed against the inner peripheral surface of the containing part 54. This closes the communication of the inner hole of the outer needle 14 through the containing part 54 of the outer needle hub 16. As a result, blood leak through the outer needle 14 with the inner needle 10 retracted can be prevented.

Then, in carrying out a procedure of fluid or blood transfusion after removal of the inner needle 10, a syringe chip and the like for example, not shown in figures, is inserted into the containing part 54 via the proximal end-side opening 40 of the outer needle hub 16, said chip pressing the open-close part 80 of the hemostasis valve 76 toward the distal end of the outer needle hub 16. This allows the cut 84 of the open-close part 80 to be pushed open with the end part of the tapered cylinder of the pusher 88, while elastically deforming the cylindrical part 82 in a contracting way, to engage the inner surface of the cut 84 with the outer peripheral surface of such end part. The cut 84 is thereby maintained open. Then, the procedure of liquid or blood transfusion starts.

Figure 5:
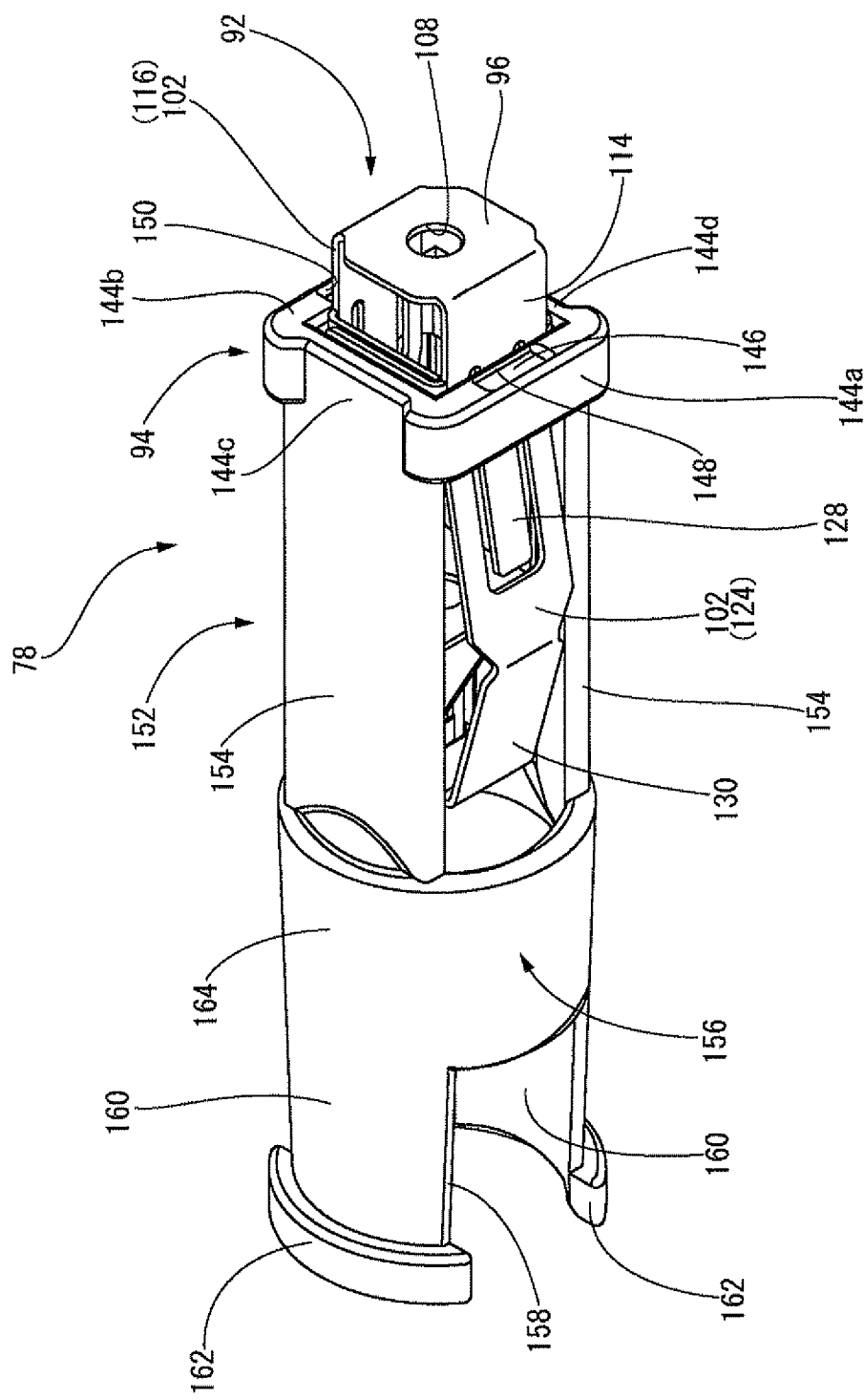
FIG. 5 is an explanatory axonometric view showing a specific example of a needle tip protector having a structure according to this invention possessed by the indwelling needle assembly shown in FIG. 1.

On the other hand, the needle tip protector 78 contained in the cylindrical containing part 34 of the inner needle hub 12 comprises, as shown in FIGS. 1, 2 and 5, a protector main body 92 and an action ring 94 externally fitted about said protector main body 92.

The protector main body 92 comprises a metal single unit made by flexurally deforming, at various part, a thin metal plate cut out in a given shape. As the metal material that forms the protector main body 92, the one that exerts elasticity in a form of a plate is used. For example, metal materials such as stainless steel, aluminum, aluminum alloys, titanium, titanium alloys, copper, copper alloys are available for use.

As evident from FIGS. 6 through 11, the protector main body 92 made of a metal single unit as a whole is in an approximate form of a square cylinder with a bottom extending along the central axis (shown as P in FIGS. 8 and 10) and integrally comprising two side plates that are a proximal end-side bottom plate 96 and a distal end-side bottom plate 98, as well as four side plates, that are, a first flexible side plate 100 and a second flexible side plate 102 as the flexible plate, a first parallel side plate 104, and a second parallel side plate 106.

The proximal end-side bottom plate 96 and distal end-side bottom plate 98, as insertion passage formation walls, are in forms of two rectangular plates with approximately the same size and are arranged so as to face each other at a given distance in the direction of the central axis P of the protector main body 92 that coincides with the axial direction of the inner needle 10 and intersect with the central axis P. In the protector main body 92, the proximal end-side bottom plate 96 is arranged in place on the proximal end side, and the distal end-side bottom plate 98 on the distal end side. At the center of the proximal end-side bottom plate 96 and distal end-side bottom plate 98, a first insertion hole 108 and a second insertion hole 110 are formed respectively as insertion passages having a form of a through-hole. As evident from FIG. 10, the first insertion hole 108 made in the proximal end-side bottom plate 96 and the second insertion hole 110 made in the distal end-side bottom plate 98 are placed to locate themselves on the same axis, both having a circular form with a larger diameter than the outer diameter of the inner needle 10 (shown by two-dotted lines in FIG. 10). Then, the diameter of the first insertion hole 108 is made smaller than the outer diameter of the above engaging part 20 provided in the inner needle 10, whereas the diameter of the second insertion hole 110 is made larger than the outer diameter of the engaging part 20. Since the distal end-side bottom plate 98 is located on the distal end side from the proximal end-side bottom plate 96 in the axial direction of the inner needle 10, the part closer to the needle tip 18 of the inner needle 10 than the insertion point into the first insertion hole 108 is inserted into the second insertion hole 110.

This allows the protector main body 92 to be mounted to the inner needle 10 in a movable way in the needle axis direction under the state where it extends in the needle axis direction with its central axis P aligned with the axial direction of the inner needle 10 by having the inner needle 10 inserted into the insertion holes 108 and 110 of the distal end-side and proximal end-side bottom plates 96 and 98 respectively. Then, when the protector main body 92 is moved in the axial direction of the inner needle 10, the inner needle 10 slides over the inner peripheral surfaces of the first and second insertion holes 108 and 110, and during such sliding movement, the engaging part 20 of the inner needle 10 passes through the second insertion hole 110 of the distal end-side bottom plate 98 without being able to pass through the first insertion hole 108 of the proximal end-side bottom plate 96.

On the other hand, as evident from FIGS. 6 through 9, the first and second flexible side plates 100 and 102 and the first and second parallel side plates 104 and 106 are each in a form of a flat rectangular plate. And, they are arranged so as to extend along the central axis P enclosing such central axis P on four sides at a position orthogonally away from the central axis P of the protector main body 92.

Among these four side plates 100 to 106, the first flexible side plate 100 and the second flexible side plate 102 facing it stretch out integrally from the two edges, among the four edges of the proximal end-side bottom plate 96 in a rectangular form, that are located on both sides of the first insertion hole 108 sandwiched in between, toward the location of the distal end-side bottom plate 98. In other words, a metal plate flexurally deformed in a C-shape is configured by the first flexible side plate 100, the second flexible side plate 102 and the proximal end-side bottom plate 96.

Figure 10:
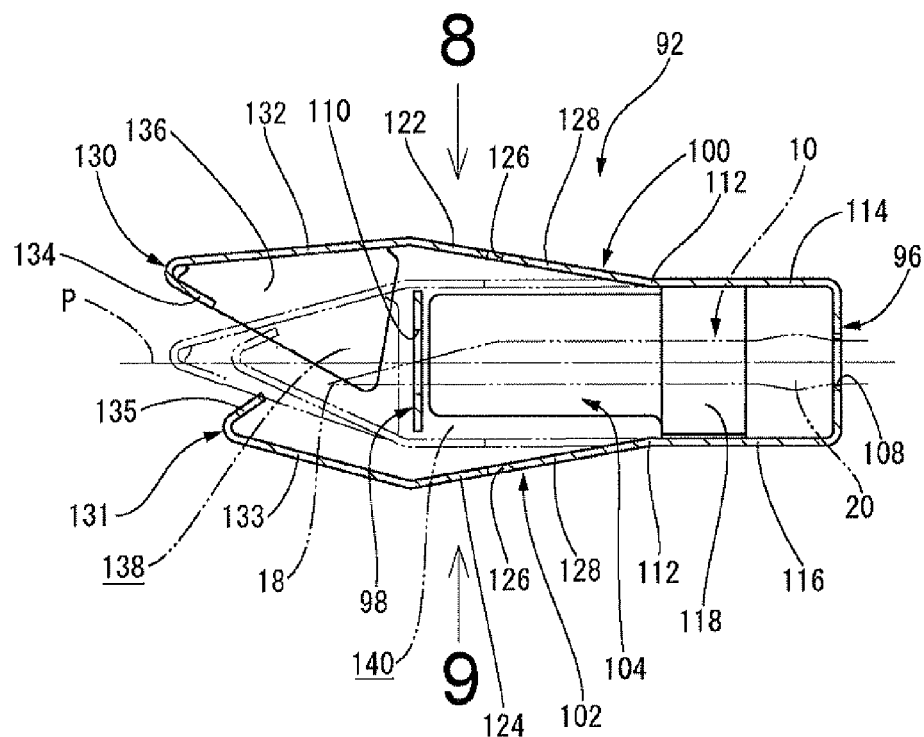
FIG. 10 is a cross-section diagram cut through 10-10 in FIG. 8.
Figure 11:
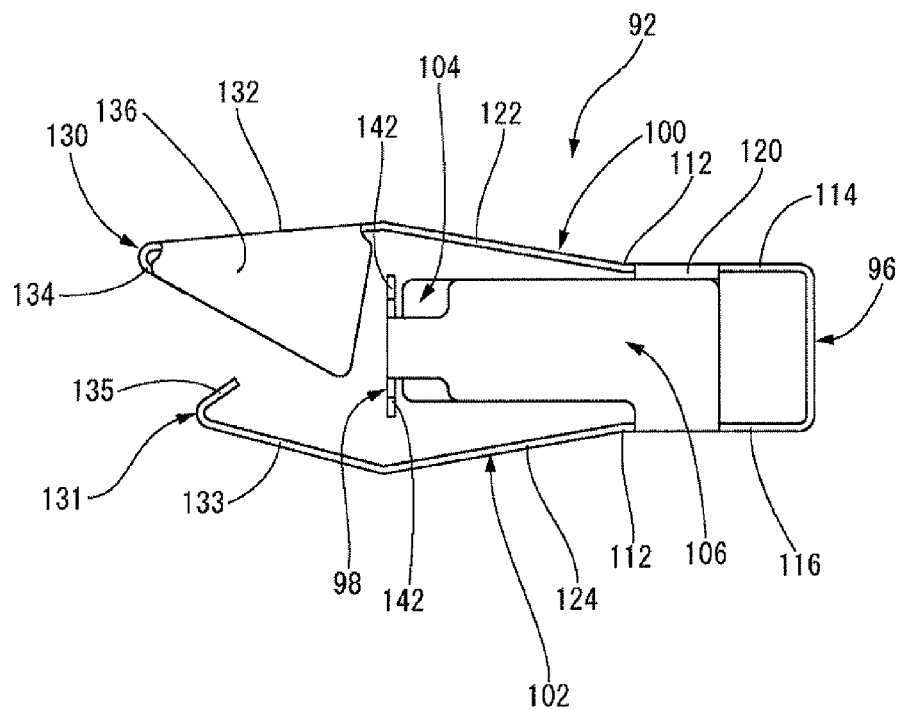
FIG. 11 is a diagram view indicated by the arrow 11 in FIG. 8.

Also, as evident from FIGS. 10 and 11, the first flexible side plate 100 and second flexible side plate 102 are each provided with a bent part 112 in the middle portion in their longitudinal direction, each of said flexible side plates 100 and 102 being bent outward from the protector main body 92 in a relatively gradual obtuse angle. This makes the proximal end side portion of each bent part 112 of the first flexible side plate 100 and second flexible side plate 102 to be a first parallel extension part 114 and a second parallel extension part 116 respectively, each extending parallel in the direction of the central axis P.

At the edge on both sides of this first parallel extension part 114 in the cross direction, a first stopper plate 118 and a second stopper plate 120 extending out integrally toward the second parallel extension part 116 are integrally provided facing each other. These first stopper plate 118 and second stopper plate 120 get butted against or in contact with the inner surface of the second parallel extension part 116 when an acting force is applied to the outer surface of the first parallel extension part 114 and second parallel extension part 116 to press them toward the central axis P of the protector main body 92. This prevents each of the parallel extension parts 114 and 116 from undergoing flexural and elastic deformation in the direction of getting closer to the central axis P. The stopper mechanism comprises these first stopper plate 118 and second stopper plate 120.

On the other hand, each part of the first flexible side plate 100 and second flexible side plate 102 closer to the distal end-side than each bent part 112 is tilted so as to gradually get away from the central axis P of the protector main body 92 as it extends toward the distal end-side bottom plate 98, that is, to increase the distance between the two facing surfaces. And, the tilted part closer to the distal end-side than the bent part 112 of the first flexible side plate 100 is made to be a first flexible piece 122, whereas the tilted part closer to the distal end-side than the bent part 112 of the second flexible side plate 102 is made to be a second flexible piece 124. Since flexural and elastic deformation of each of the parallel extension parts 114 and 116 toward the central axis P is prevented, as mentioned above, the first flexible piece 122 and second flexible piece 124 are each subjected to flexural and elastic deformation so as to rotate inward of the protector main body 92 centering on the bent part 112 when an acting force is applied to the first flexible piece 122 and second flexible piece 124 to press them toward the central axis P of the protector main body 92. In other words, the first and second flexible pieces 122 and 124 are configured to be able to undergo flexural and elastic deformation in the direction of bringing their tips closer to the central axis P.

Figure 6:
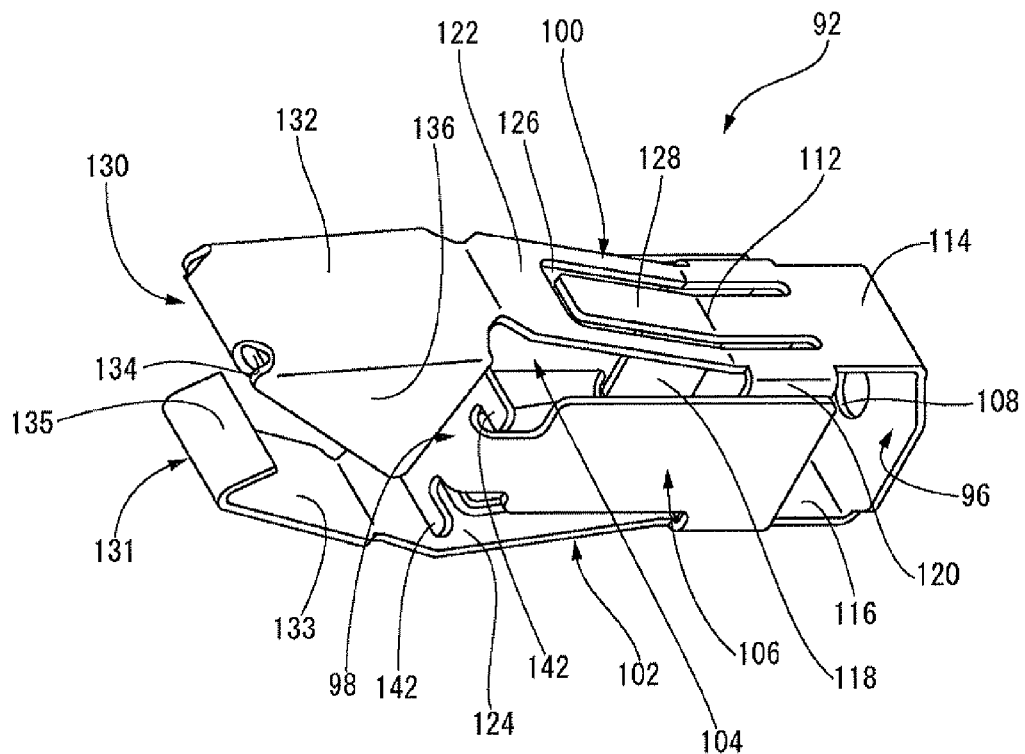
FIG. 6 is an explanatory axonometric view showing a protector main body comprising the needle tip protector shown in FIG. 5.
Figure 7:
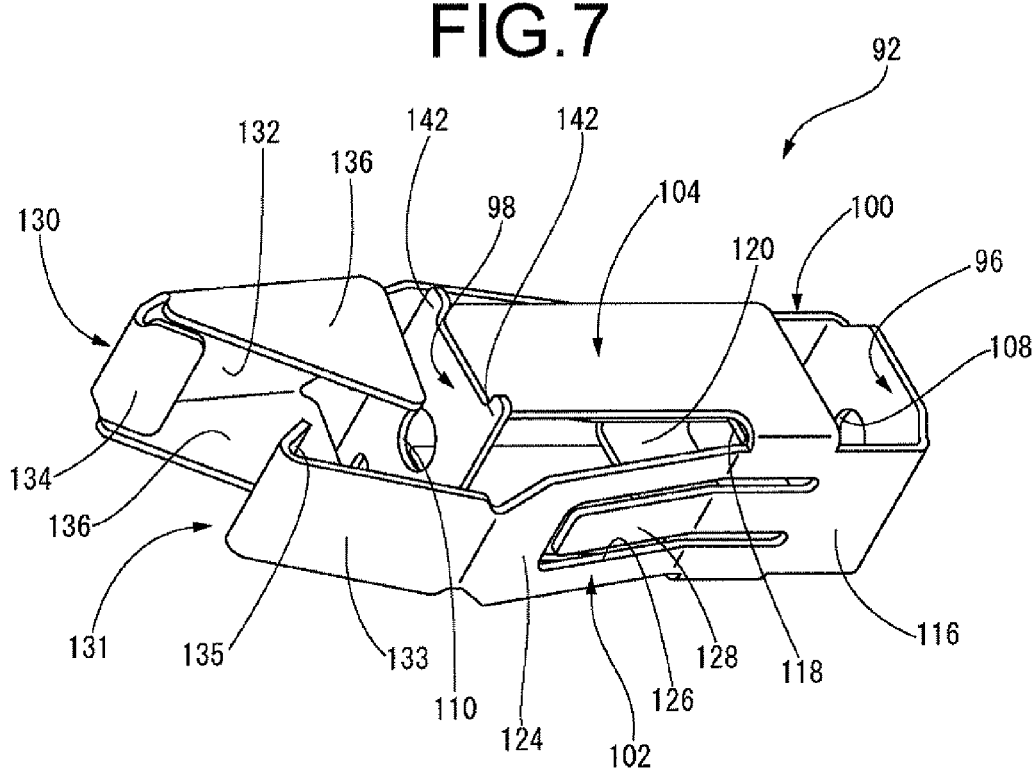
FIG. 7 is an explanatory axonometric view different from FIG. 6 showing the protector main body comprising the needle tip protector shown in FIG. 5.

As shown in FIGS. 6 and 7, a slot 126 in a C-shape is formed in each of the first flexible side plate 100 and second flexible side plate 102 that extends in the longitudinal direction across from the parallel extension parts 114 and 116 on the side closer to the proximal end than the bent part 112 all the way to the flexible pieces 122 and 124 on the side closer to the distal end than the bent part 112, and opens up toward the proximal end-side bottom plate 96. This forms an anti-retraction tab 128 comprising an elongated rectangular flat plate enclosed by the C-shaped slot 126 that is tilted outward from the protector main body 92 in the same direction and angle as each of the flexible pieces 122 and 124 and extends out integrally from each of the parallel extension parts 114 and 116. In other words, in each of the first and second flexible pieces 122 and 124 (the first and second flexible side plates 100 and 102), the anti-retraction tab 128 comprising an elongated rectangular flat plate is formed by a cut-and-raise processing. This allows each of the anti-retraction tabs 128 to be independent from each of flexible pieces 122 and 124 and be able to undergo flexural and elastic deformation in the direction of getting closer to the central axis P.

Figure 8:
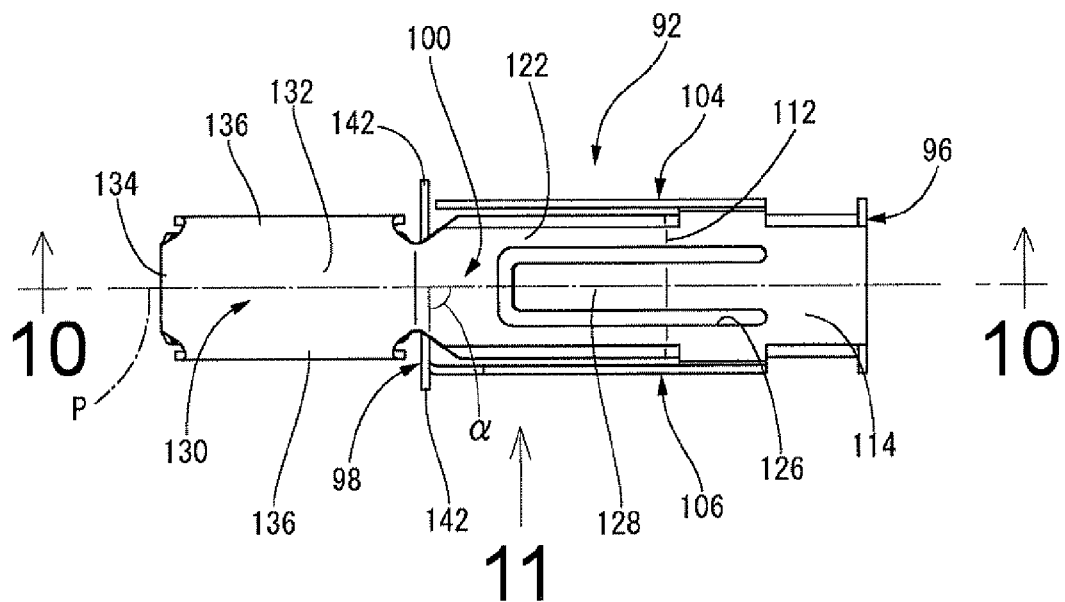
FIG. 8 is a front-view diagram for explaining the protector main body shown in FIG. 6 which represents the view indicated by the arrow 8 in FIG. 10.

At the distal end of the first and second flexible pieces 122 and 124, protection parts 130 and 131 are integrally formed respectively. As shown in FIG. 8, each of the protection parts 130 and 131 is in a bent plate form integrally provided with first protection plates 132 and 133 extending slantedly from the distal end of each of the flexible pieces 122 and 124 to the opposite side of the above proximal end-side bottom plate 96 toward the central axis P at an obtuse angle relative to each of the flexible pieces 122 and 124 as well as second protection plates 134 and 135 extending slantedly from the distal end of said protection parts 130 and 131 toward the location of the above proximal end-side bottom plate 96 getting closer to the central axis P at an acute angle relative to each of the first protection plates 132 and 133.

And, the second protection plates 134 and 135 as well as the first protection plates 132 and 133 of such protection parts 130 and 131 have all the same width, although the extension lengths of the former are made substantially smaller than those of the latter. This allows each distal end of the second protection plates 134 and 135 of the protection parts 130 and 131 provided at the first and second flexible pieces 122 and 124 to be placed at a location separated from the central axis P of the protector main body 92 by a given distance toward where each of the flexible pieces 122 and 124 is located. Also, the extension length of the first protection plate 132 of the protection part 130 provided at the first flexible piece 122 of the first flexible side plate 100 is made longer by a given dimension than that of the first protection plate 133 of the protection part 131 provided at the second flexible piece 124 of the second flexible side plate 102.

In addition, at the edge on both sides, in the cross direction, of the first protection plate 132 of the protection part 130 of the first flexible piece 122, a lateral lid plate 136 is integrally formed, one at each edge. This lateral lid plate 136 is made in a form of a triangle that has two oblique sides in about the same length as the first protection plate 132, wherein the angle formed by the two oblique sides is about the same as the tilt angle of the second protection plate 134 relative to the first protection plate 132. Then, these two lateral lid plates 136 and 136 are integrally formed so as to suspend down from the edge on both sides, in the cross direction, of the first protection plate 132 under the state of facing each other on both sides, in the cross direction, sandwiching the protection part 130 of the first flexible piece 122 in between and positioning one of the oblique sides against the side surface of the first protection plate 132 of the protection part 130. This allows each of the lateral openings that open up to both sides, in the cross direction, of the protection part 130 in a bent form of the first flexible piece 122 to be covered with two lateral lid plates 136 and 136.

Therefore, when the first flexible piece 122 of the first flexible side plate 100 and the second flexible piece 124 of the second flexible side plate 102 each undergo flexural and elastic deformation at the same time in the direction of bringing their edge closer to the central axis P of the protector main body 92, that is, inward of the protector main body 92, the protection parts 130 and 131 that are each provided at each edge of the flexible pieces 122 and 124 get closer to each other, as shown by the two-dotted line in FIG. 10, and the distal end of the second protection plate 135 of the protection part 131 of the second flexible piece 124 is gradually brought to a position in contact with, or immediately prior to such contact with, the first protection plate 132 of the protection part 130 of the first flexible piece 122. At that time, a distal end-side closed space 138 in an approximate form of a triangular prism is formed enclosed by the distal end-side bottom plate 98, the protection parts 130 and 131 of the first and second flexible pieces 122 and 124 respectively, the two lateral lid plates 136 and 136 provided at the protection part 130 of the first flexible piece 122 on the side closer to the distal end than the distal end-side bottom plate 98 of the protector main body 92. Also, on the side closer to the proximal end than the distal end-side bottom plate 98 of the protector main body 92, a proximal end-side closed space 140 is made to form as a housing part in an approximate form of an elongated rectangle enclosed by the distal end-side and proximal end-side bottom plates 96 and 98 and the four side plates 100 to 106.

Figure 9:
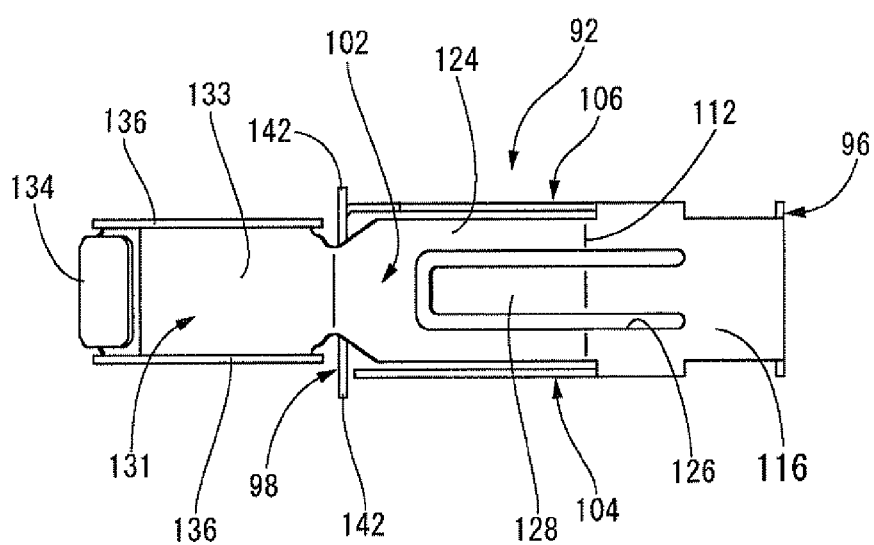
FIG. 9 is a rear-view diagram for explaining the protector main body shown in FIG. 6 which represents the view indicated by the arrow 9 in FIG. 10.

As shown in FIGS. 8 and 9, the first parallel side plate 104 and second parallel side plate 106 extend out straight, without having any bent part that bends them outward from the protector main body 92, unlike the first and second flexible side plates 100 and 102, from the arranged location of the parallel extension parts 114 and 116 of the first and second flexible side plates 100 and 102 toward each of the flexible pieces 122 and 124 in the direction of the central axis P of the protector main body 92. These first parallel side plate 104 and second parallel side plate 106 are placed facing each other in the direction orthogonal to the facing direction of the first flexible side plate 100 and second flexible side plate 102 at about the same distance apart as each width thereof and outside of the first and second stopper plates 118 and 120 sandwiched in between. Under such arrangement conditions, the first parallel side plate 104 and second parallel side plate 106 are, at each proximal end-side part, integrally connected to the edge on both sides, in the cross direction, of the second parallel extension part 116 of the second flexible side plate 102. This allows the first parallel side plate 104 and second parallel side plate 106 to be integrally formed with the proximal end-side bottom plate 96 via the second flexible side plate 102.

Then, the distal end-side bottom plate 98 is integrally formed with the distal end of the second parallel side plate 106. This distal end-side bottom plate 98 extends out in the direction orthogonal to the central axis P of the protector main body 92 to bridge across the first parallel side plate 104 and second parallel side plate 106. In other words, the length of the second parallel side plate 106 is made larger than that of the first parallel side plate 104 by a given dimension, and the distal end-side part of the second parallel side plate 106 is bent inward of the protector main body 92 at about a right angle and extended toward the first parallel side plate 104 so as to make both lengths equal. That way, the distal end-side bottom plate 98 in a form of a rectangular flat plate is formed at the bend of the second parallel side plate 106.

As evident from FIGS. 6 through 9, at the four corners of such distal end-side bottom plate 98 in a form of a rectangular flat plate, a protruded engaging part 142 is integrally formed, one at each corner. This protruded engaging part 142 is made in a form of a small plate integrally protruding by the same lengths from both ends of the two edges (sides) in the longitudinal direction of the distal end-side bottom plate 98 located on both sides in the facing direction of the first parallel side plate 104 and second parallel side plate 106. In other words, these protruded engaging parts 142 are integrally provided to the distal end-side bottom plate 98 that is integrally formed with the second parallel side plate 106 and extend out from the outer surface opposite to the facing side of the first parallel side plate 104 and second parallel side plate 106 in the direction orthogonal to the central axis P outward from the protector main body 92.

Figure 12:
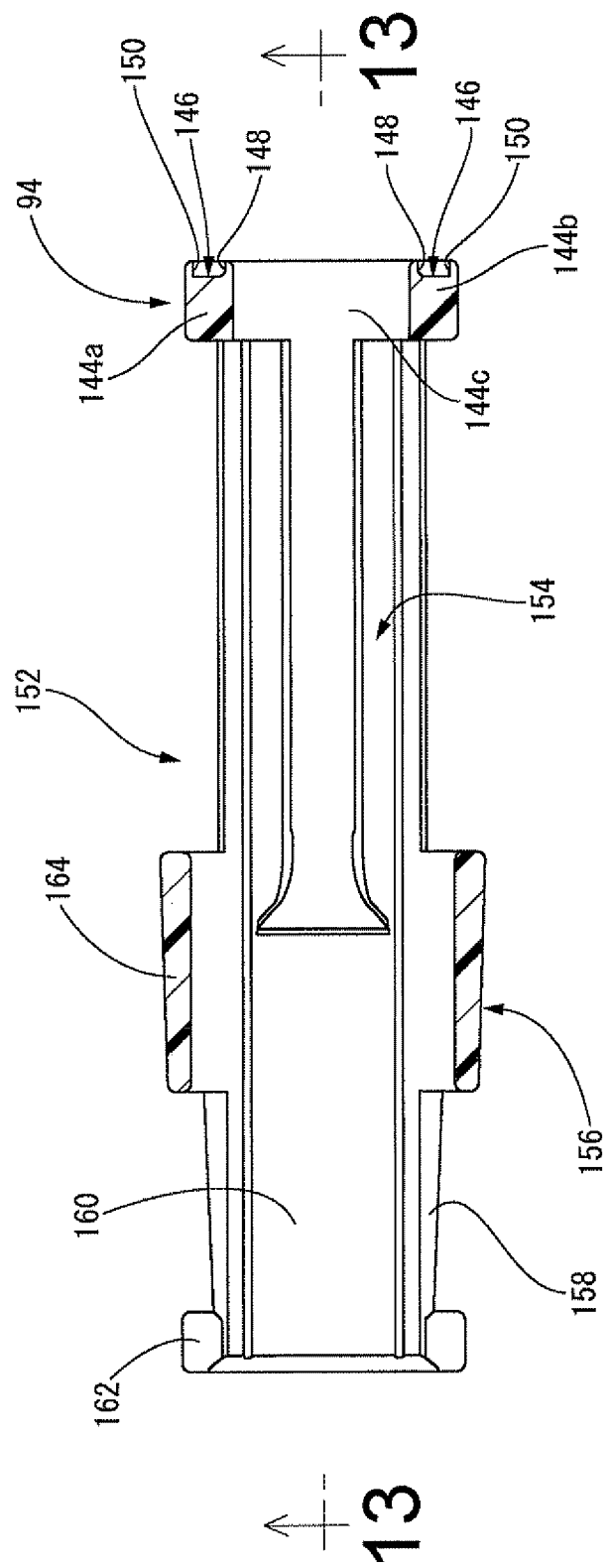
FIG. 12 is a longitudinal cross section diagram for explaining an action ring comprising the needle tip protector shown in FIG. 5 which represents the section view taken along line 12-12 in FIG. 13.
Figure 13:
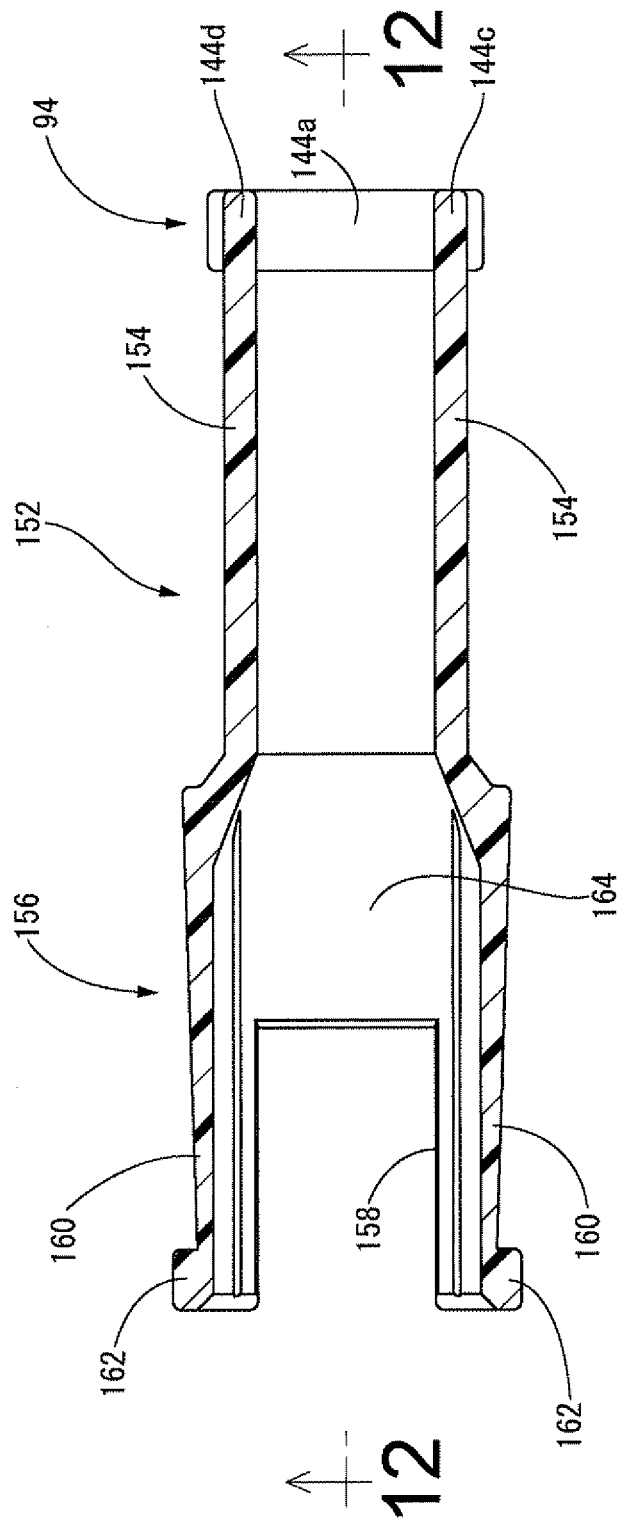
FIG. 13 is a section diagram taken along line 13-13 in FIG. 12.

On the other hand, the action ring 94 externally fitted about the protector main body 92 has, as shown in FIGS. 5, 12 and 13, a frame form made of a rectangular inner hole by combining, in a rectangular form, a first side wall 144a and a second side wall 144b facing each other, and a third side wall 144c and a fourth side wall 144d facing each other in the direction orthogonal to the facing direction of the first and second side walls 144a and 144b. Then, the distance between the facing surfaces of the first side wall 144a and second side wall 144b is made slightly larger than the widths of the first and second parallel side plates 104 and 106, whereas the distance between the facing surfaces of the third and fourth side walls 144c and 144d is made slightly larger than the widths of the first and second flexible side plates 100 and 102.

The first side wall 144a and second side wall 144b is in an approximate form of a thick rectangular plate or a prism. At the center of each end surface of these first and second side walls 144a and 144b located on one side in the axial direction of the action ring 94, a recessed groove 146 with a rectangular cross section is formed extending in the longitudinal direction of each of the side walls 144a and 144b. In other words, two recessed grooves 146 and 146 are provided on the end surface on one side in the axial direction of the action ring 94, apart from each other in the circumferential direction and extending along the periphery. Meanwhile, each recessed groove 146 has width and length that allows the distal end of the above anti-retraction tab 128 to thrust into it. And, among the four side surfaces of each recessed groove 146, the side surface located on the inner hole side of the action ring 94 extending along the periphery thereof is made to be a first engaging surface 148, and the other side surface opposing to the first engaging surface 148 is made to be a second engaging surface 150.

On the other hand, the third side wall 144c and fourth side wall 144d are made in a form of a rectangular plate thinner than the first and second side walls 144a and 144b. And, a latching protrusion 152 that can be elastically deformed is integrally formed with the action ring 94 so as to extend from the third and fourth side walls 144c and 144d in the direction opposite to the side where the above recessed groove 146 of the action ring 94 is formed.

The proximal end-side part of the latching protrusion 152 extending out from the action ring 94 comprises two flat plates 154 and 154, and their distal end side portion comprises a cylindrical part 156 integrally connected to each end surface of the two flat plates 154 and 154 on the side surface on one side in the axial direction. The two flat plates 154 and 154 are each in a form of an elongated rectangular flat plate facing each other in the same direction as the facing direction of the third and fourth side walls 144c and 144d.

The cylindrical part 156, as mentioned later, has an inner diameter that allows the protector main body 92 to pass through it without touching the inner periphery, that is, an inner diameter that does not interfere with the protector main body 92. Also, at two locations facing each other in the diameter direction on the distal end side of this cylindrical part 156, rectangular cutout portions 158 and 158 are each provided. This allows each of extended latching pieces 160 and 160 in a divided cylindrical form to be formed, in the two remaining spaces on the distal end side portion of the cylindrical part 156 where two cutout portions 158 and 158 are provided, extending in the axial direction and made to be elastically deformable inward in the diameter direction. Further, a projected latching rim 162 of outer flange shape is integrally provided to the outer periphery of the distal end of each extended latching piece 160.

Moreover, due to the two cutout portions 158 and 158 provided on the distal end side of the cylindrical part 156, the proximal end side portion, which is the connection side of the two flat plates 154 and 154 of the cylindrical part 156 is made to be a circular reinforcing part 164. In other words, the latching protrusion 152 extending out from the action ring 94 is provided with the circular reinforcing part 164 in the middle portion of its extending direction, and two flat plates 154 and 154 extend out facing each other from one end surface of this circular reinforcing part 164 in the axial direction, whereas two extended latching pieces 160 and 160 extend out facing each other in the axial direction from the other end surface of the circular reinforcing part 164 in the same direction. This allows the free length of each extended latching piece 160 to be favorably short even if the overall length of the latching protrusion 152 is made large enough. As a result, reinforcement of each extended latching piece 160, and even the latching protrusion 152, is favorably enhanced.

Meanwhile, the material of such action ring 94 is not limited to any particular one, but as mentioned later, it can be any material as long as it is capable of flexurally and elastically deform each of the flexible pieces 122 and 124 and each anti-retraction tab 128 by resisting their urging forces. However, in the present embodiment, the latching protrusion 152 deemed desirable to have elasticity is integrally formed with the action ring 94. Therefore, as the forming material of the action ring 94, resins, metals, rubbers or elastomers and the like having elasticity, for example, are used as appropriate.

And, as shown in FIG. 5, the action ring 94 is externally fitted about the proximal end side portion of the protector main body 92. In other words, the protector main body 92, except its proximal end side portion, is inserted between the two flat plates 154 and 154 of the latching protrusion 152 that is integrally formed with the action ring 94. In the protector main body 92 inserted between these two flat plates 154 and 154, the first and second flexible plates 100 and 102 are arranged to face each other in the direction orthogonal to the facing direction of the two flat plates 154 and 154 in order to avoid touching any of these. This way, the needle tip protector 78 is configured as a component to be assembled with the protector main body 92 and the action ring 94.

And, as shown in FIGS. 1 and 2, the needle tip protector 78 is mounted to the inner needle 10 in a movable way in the needle axis direction (which coincides with the central axis P of the protector main body 92) by means of having the proximal end side portion of the inner needle 10 extend out from the distal end of the inner needle hub 12 and inserted into each of the first and second insertion holes 108 and 110 made through the proximal end-side and distal end-side bottom plates 96 and 98 of the protector main body 92. Under such conditions of being mounted to the inner needle 10, the needle tip protector 78 is contained in place in the cylindrical containing part 34 of the inner needle hub 12. The needle tip protector 78 contained in the cylindrical containing part 34 is arranged in such a way that the action ring 94 is placed in contact or not in contact with the inner peripheral surface of the cylindrical containing part 34, and each of the protection parts 130 and 131 of the protector main body 92 is placed in contact or not in contact with the inner surface of a multitude of protruded plates 38.

And, while the inner needle 10 is inserted into the outer needle 14, a multitude of protruded plates 38 of the inner needle hub 12 are inserted into the proximal end-side opening 40 of the outer needle hub 16 so that the inner needle hub 12 is assembled with the outer needle hub 16. This forms an indwelling needle assembly made by assembling the inner needle hub 12 and outer needle hub 16 with each other, and within such indwelling needle assembly, the hemostasis valve 76 and needle tip protector 78 are each assembled in the state of being contained in the containing part 54 of the outer needle hub 16 and the cylindrical containing part 34 of the inner needle hub 12.

In the assembly of the inner needle hub 12 and outer needle hub 16, the latching protrusion 152 of the action ring 94 of the needle tip protector 78 extends out into the containing part 54 of the outer needle hub 16 via the distal end-side opening 28 of the cylindrical containing part 34 of the inner needle hub 12. Then, each projected latching rim 162 of the two extended latching pieces 160 and 160 of the latching protrusion 152 thrusts into the annular groove 70 provided along the inner peripheral surface of the containing part 54 to be latched to the tapered latch surface 72 of such annular groove 70.

Thus, an indwelling needle assembly comprising the above structure is used in the procedure of inserting the outer needle 14 into, and leaving it in, the blood vessel of the patient and others when fluid or blood transfusion is carried out. Next, how to use the indwelling needle assembly will be explained in detail.

First, as shown in FIG. 1, assemble the inner needle hub 12 and outer needle hub 16, and insert the inner needle 10 and outer needle 14 into the blood vessel of the patient and others under the state where the inner needle 10 is inserted into the outer needle 14.

Then, retract the inner needle 10 from the outer needle 14 by pulling back the inner needle hub 12 to retract it from the containing part 54 of the outer needle hub 16. By doing this, only the outer needle 14 is left inserted in the blood vessel of the patient and others. At this time, the cut 84 of the hemostasis valve 76 within the containing part 54 of the outer needle hub 16 is closed to prevent the patient's blood from leaking out via the outer needle 14. Also, the needle tip protector 78 mounted to the inner needle 10 and contained in the cylindrical containing part 34 of the inner needle hub 12 is prevented from moving because the projected latching rim 162 of each extended latching piece 160 at the latching protrusion 152 of the action ring 94 is latched to the annular groove 70 (tapered latch surface 72) of the containing part 54. Therefore, the inner needle 10 moves back relative to the needle tip protector 78 toward the operator.

Figure 14:
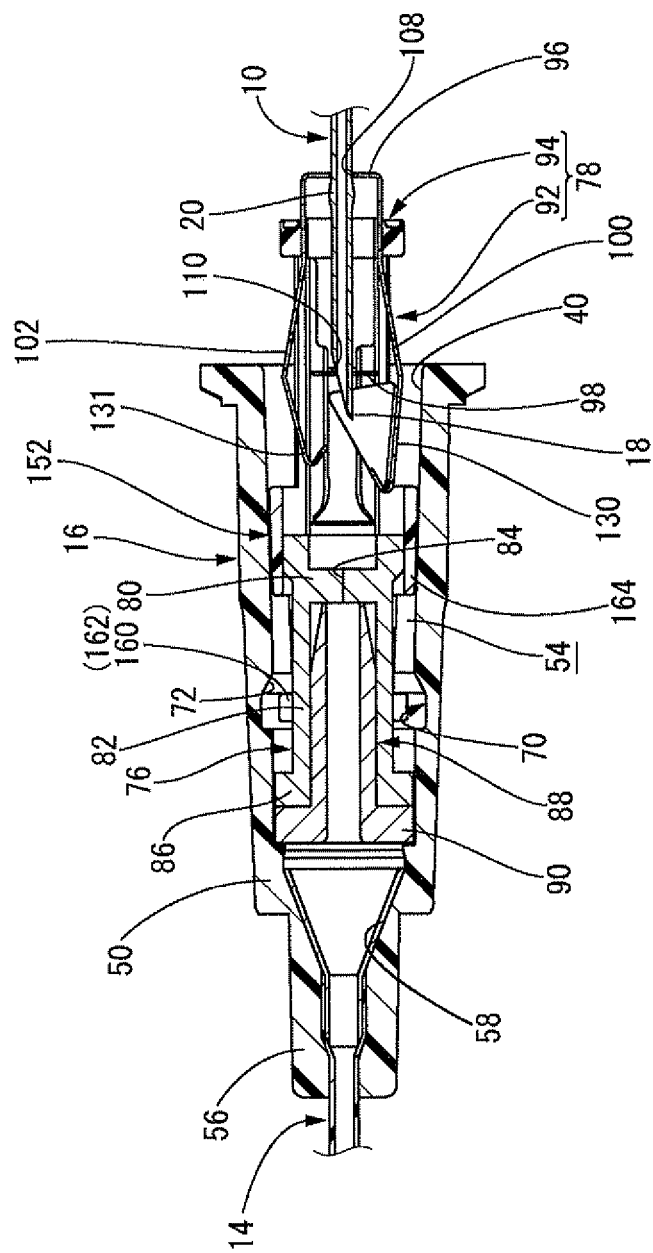
FIG. 14 is a diagram for explaining a usage of an indwelling needle assembly having a structure according to this invention, which indicates a state where the inner needle is retracted and its distal end is encased within the protector main body.

Further, as shown in FIG. 14, when the engaging part 20 provided on the side of the needle tip 18 of the inner needle 10 passes through the large-diameter second insertion hole 110 of the distal end-side bottom plate 98 of the protector main body 92 and reaches the position where the proximal end-side bottom plate 96 is placed, said engaging part 20 is engaged with the periphery of the opening of the first insertion hole 108 of the proximal end-side bottom plate 96 without passing through it. At this time, the part closer to the proximal end-side than the needle tip 18 of the inner needle 10 is placed between the facing surfaces of the proximal end-side bottom plate 96 and the distal end-side bottom plate 98 of the protector main body 92, while the needle tip 18 is placed between the two protection parts 130 and 131, each provided at the distal end of the first and second flexible pieces 122 and 124 respectively.

Figure 15:
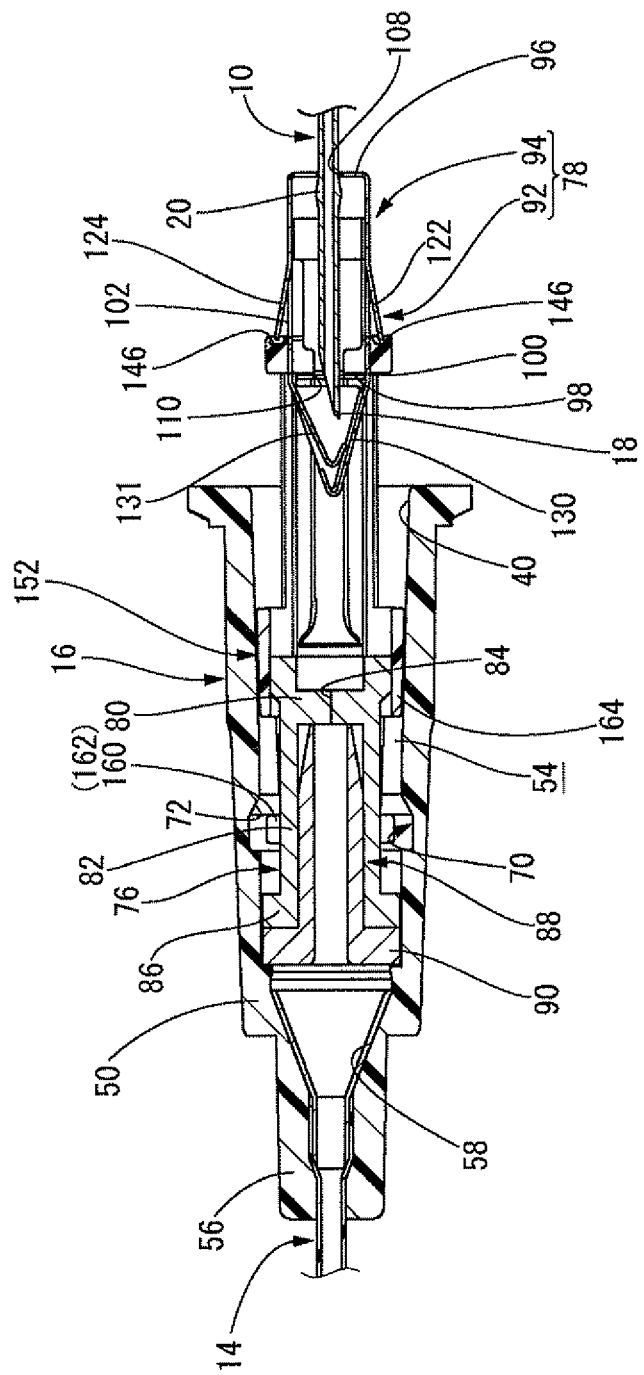
FIG. 15 is a diagram for explaining another usage of an indwelling needle assembly having a structure according to this invention, which indicates a state where the protector main body is retracted together with the inner needle to protect the distal end thereof.

And, when the inner needle 10 is further retracted back from that state, as shown in FIG. 15, the protector main body 92 engaged with the engaging part 20 of the inner needle 10 moves back, together with the inner needle 10, toward the proximal end-side opening 40 of the outer needle hub 16.

At this time, the action ring 94 externally fitted about the protector main body 92 remains at the position where the projected latching rim 162 of each extended latching piece 160 of the latching protrusion 152 thrusts into the annular groove 70, without moving over yet due to the engagement of the latching protrusion 152 with the annular groove 70. Therefore, the protector main body 92 moves relative to the action ring 94, which makes the action ring 94 move toward the distal end of the protector main body 92 while sliding over the outer periphery of the four side plates 100 to 106 of the protector main body 92. During this process, the action ring 94 presses each of the first flexible piece 122 and anti-retraction tab 128 of the first flexible side plate 100 as well as the second flexible piece 124 and anti-retraction tab 128 of the second flexible side plate 102 of the protector main body 92 in the direction of getting closer to the inner needle 10 on the flat inner surface of the first and second side walls 144a and 144b, thereby flexurally and elastically deforming each of them in the same direction.

As a result, the distal end-side closed space 138 and proximal end-side closed space 140 are formed on the distal end-side and proximal end-side of the protector main body 92, as mentioned above. Thus, the part of the distal end of the inner needle 10 closer to the proximal end side than the needle tip 18 is housed in place in the proximal end-side closed space 140, whereas the needle tip 18 of the inner needle 10 is housed in the distal end-side closed space 138. This allows the entire distal end portion including the needle tip 18 of the inner needle 10 to be covered and protected by the protector main body 92. As evident from this description, the location where the protection parts 130 and 131 come in contact with each other due to flexural and elastic deformation of the first flexible piece 122 and second flexible piece 124 toward the direction of getting closer to each other is considered a protective position of each of the protection parts 130 and 131 in the present embodiment. Meanwhile, since the first parallel side plate 104 and second parallel side plate 106 extend out straight parallel in the direction of the central axis P of the protector main body 92, as mentioned above, they are in no way pressed inside of the protector main body 92 on the flat inner surface of the third and fourth side walls 144c and 144d of the action ring 94 during an advance movement thereof relative to the protector main body 92, and therefore, are not subject to any flexural or elastic deformation.

Figure 16:
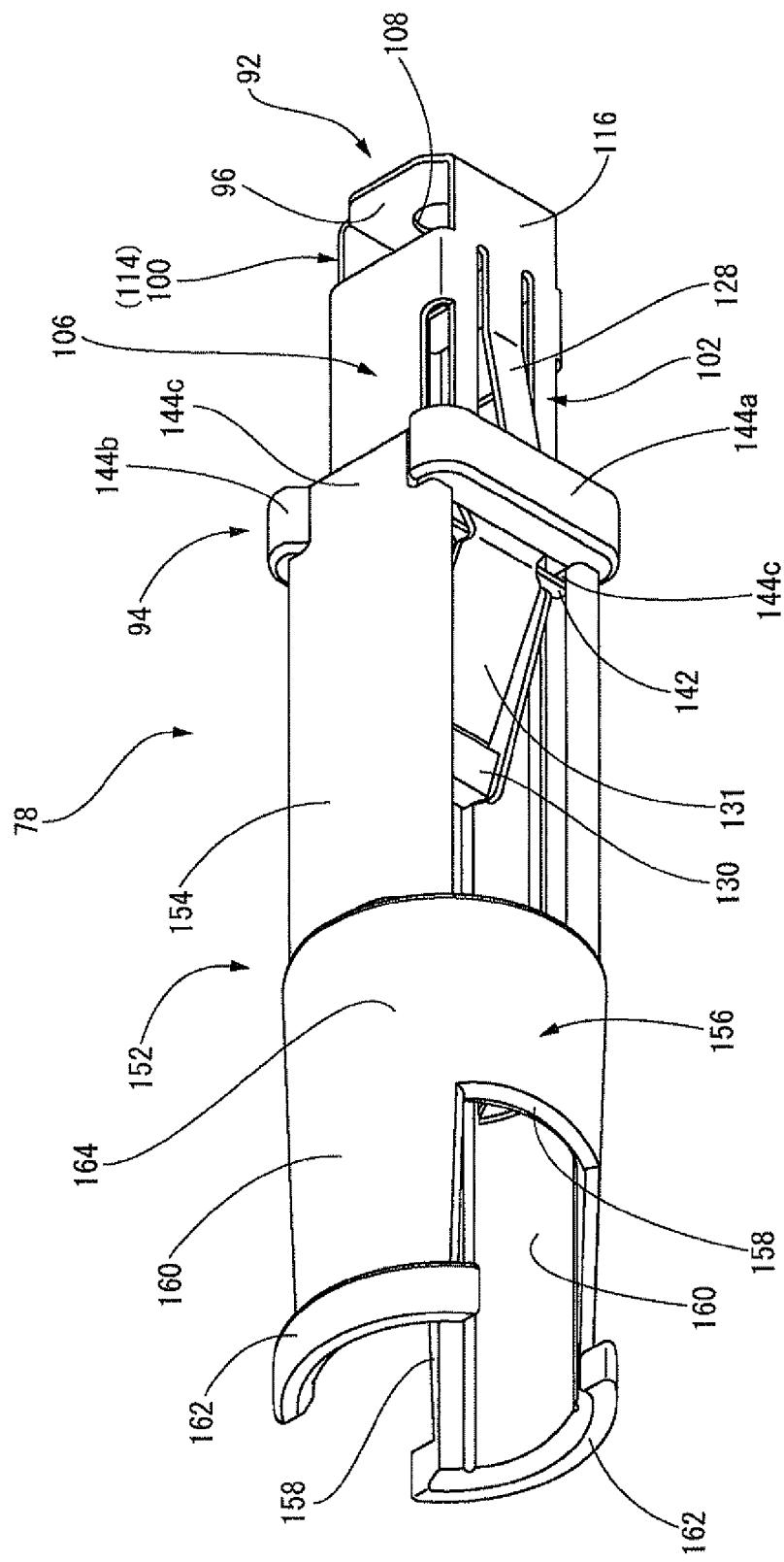
FIG. 16 is an explanatory axonometric view of a needle tip protector showing a state where the action ring is engaged with a protruded engaging part of the protector main body through an advance movement of the action ring relative to the protector main body.

Then, when the action ring 94 moves to the distal end side of the protector main body 92 until reaching the protective position where each of the protection parts 130 and 131 covers the needle tip 18 of the inner needle 10, or when the action ring 94 further moves to the distal end side of the protector main body 92 from these moved positions as shown in FIG. 16, the advance-side edge (front edge) of the action ring 94 located on the distal end side of the protector main body 92 is engaged with the four protruded engaging parts 142, 142, 142 and 142 integrally formed with the distal end-side bottom plate 98 of the protector main body 92 (FIG. 16 only shows one protruding engaging part 142 engaged with the action ring 94). This prevents the action ring 94 from advancing further, or stops the protector main body 92 from moving back relative to the action ring 94 following the retraction of the inner needle 10, which makes it possible to prevent any slip-out of the action ring 94 from the distal end side of the protector main body 92. In this way, a slip-stop mechanism, including the protruded engaging part 142, that prevents the action ring 94 from slipping out of the distal end side of the protector main body 92 is configured.

Figure 17:
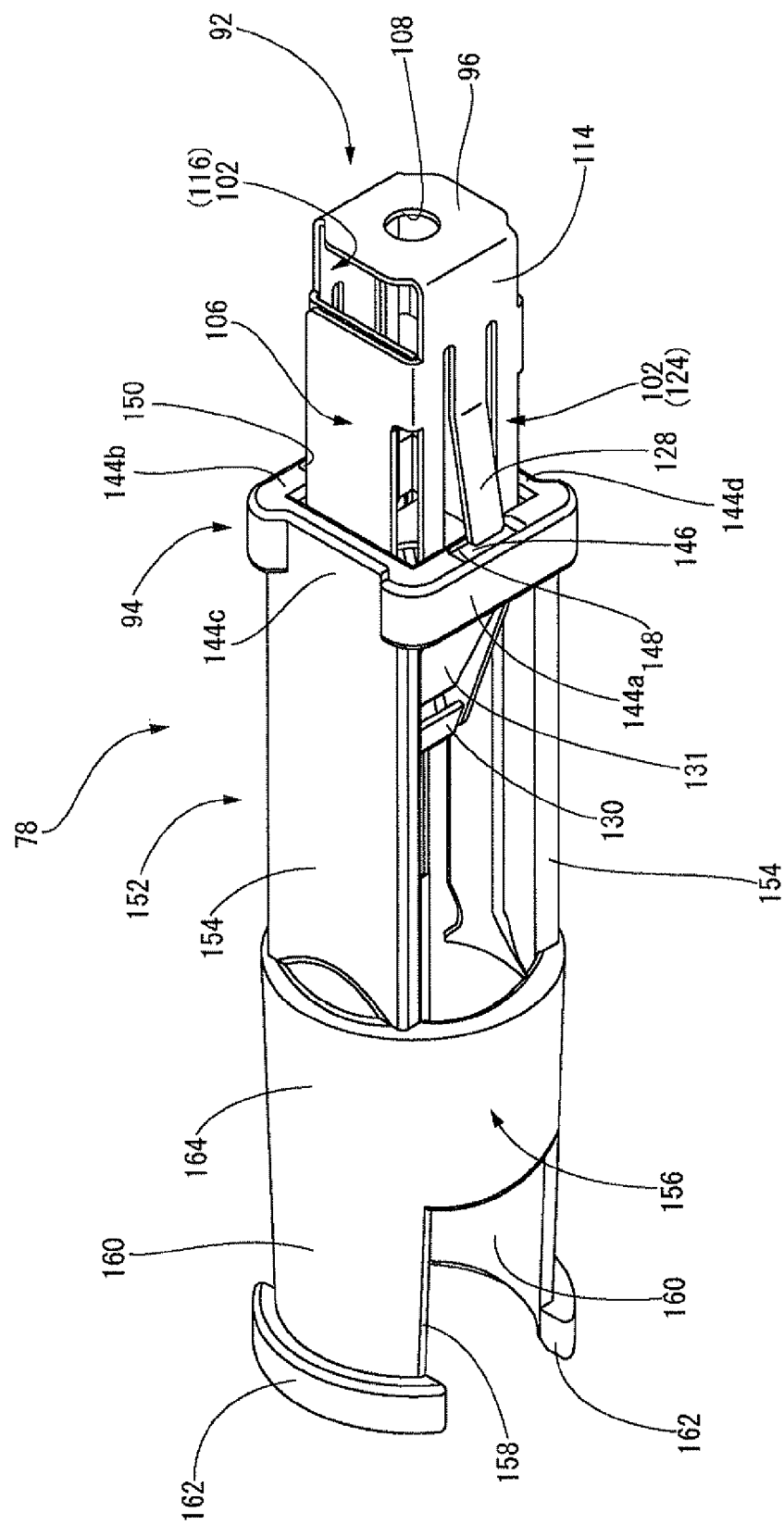
FIG. 17 is an explanatory axonometric view of a needle tip protector showing a state where an anti-retraction tab of the protector main body is engaged with a first and second engaging surfaces of the action ring through its advance movement relative to the protector main body.

Also at this time, the action ring 94 reaches a position overriding each of the anti-retraction tabs 128 and 128 of the first and second flexible pieces 122 and 124, as shown in FIGS. 15 and 17. Then, only each anti-retraction tab 128 restores from the state of elastic deformation with the state of deformation of the first and second flexible pieces 122 and 124 maintained, and the distal end of each anti-retraction tab 128 thrusts or intrudes into the recessed groove 146 provided on each rear-end surface of the first side wall 144a and second side wall 144b of the action ring 94 (the end surface located on the proximal end side of the protector main body 92).

This brings the distal end of each anti-retraction tab 128 to a state capable of engaging with the first engaging surface 148 and second engaging surface 150 composed of two inner surfaces of the recessed groove 146. By this engagement of the distal end of each anti-retraction tab 128 with the first engaging surface 148, each anti-retraction tab 128 is restricted from unnecessarily being deformed elastically in the direction of getting closer to the inner needle 10 from the state of contact with the action ring 94. Also, by the engagement of the distal end of each anti-retraction tab 128 with the second engaging surface 150, each anti-retraction tab 128 is restricted from unnecessarily being deformed elastically in the direction of getting away from the inner needle 10 from the state of contact with the action ring 94. As a result, the state of contact of each anti-retraction tab 128 with the action ring 94 is prevented from being easily released, thus blocking the retractive movement of the action ring 94 from the position where each anti-retraction tab 128 thrusts into the recessed groove 146. In this way, a slip-stop mechanism, including the anti-retraction tab 128 and the first engaging surface 148, that prevents the action ring 94 from slipping out of the proximal end side of the protector main body 92 is configured.

Figure 18:
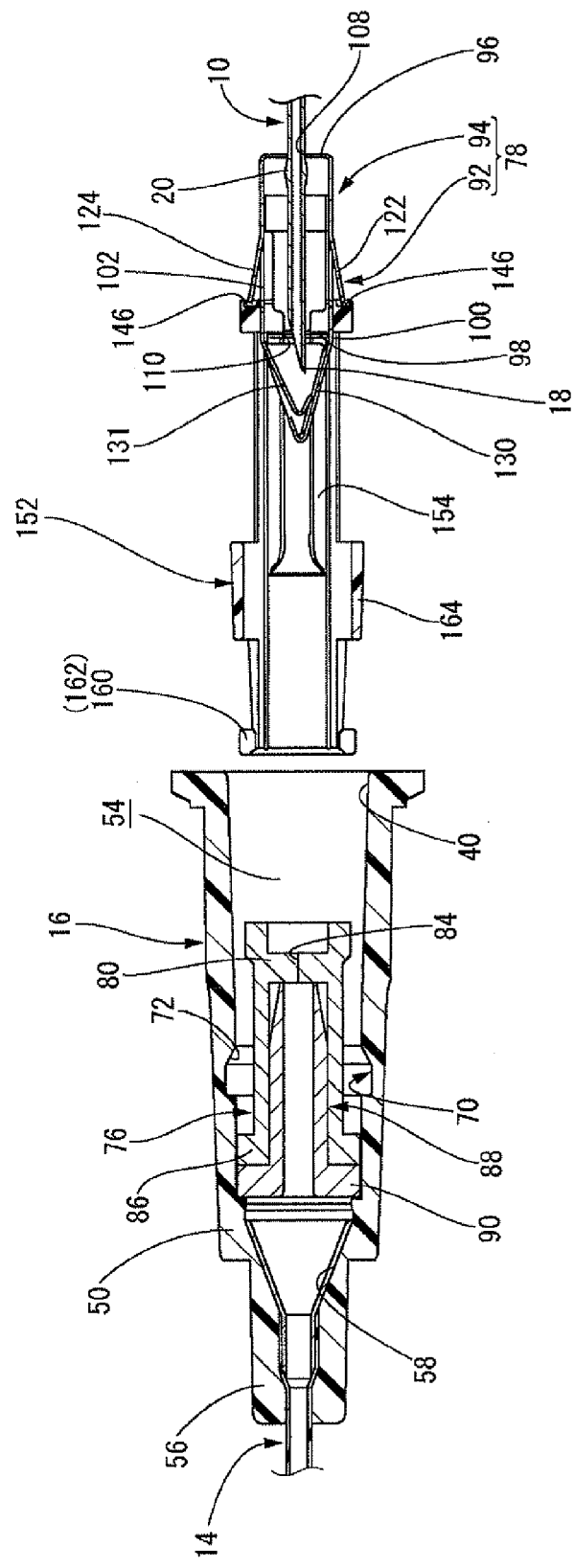
FIG. 18 is a diagram showing a usage of an indwelling needle assembly having a structure according to this invention different from those shown in FIGS. 14 and 15, which indicates a state where the inner needle with its needle tip protected by the protector main body is detached from the outer needle hub together with the needle tip protector.

Moreover, the inner needle 10 and the protector main body 92 are further moved backward together, as shown in FIG. 18, from the state where the movements of the action ring 94 relative to the protector main body 92 in both advancing and retreating directions are blocked. Then, the action ring 94 is pressed in the backward direction of the protector main body 92 at each protruded engaging part 142 thereof, and the projected latching rim 162 of each extended latching piece 160 at the latching protrusion 152 of the action ring 94 slides over the tapered latch surface 72 of the annular groove 70 formed along the inner periphery of the outer needle hub 16, thus easily releasing the state of engagement of said projected latching rim 162 with the annular groove 70. This allows the action ring 94 to integrally move backward together with the inner needle 10 and protector main body 92. Since the action ring 94 remains engaged, at this time, with each protruded engaging part 142 and each anti-retraction tab 128 of the protector main body 92, the state of having each of the flexible pieces 122 and 124 flexurally and elastically deformed by the action ring 94, that is, the state of the needle tip 18 of the inner needle 10 protected with each of the protection parts 130 and 131 is maintained.

Furthermore, the entire inner needle 10 is detached from the containing part 54 of the outer needle hub 16 together with the needle tip protector 78 by further retractive movement of the inner needle 10 while the needle tip 18 of the inner needle 10 is still protected with each of the protection parts 130 and 131 of the protector main body 92.

As evident from the above description, in the indwelling needle assembly of the present embodiment, the hemostasis valve 76 is contained in place in the containing part 54 of the outer needle hub 16, whereas the needle tip protector 78 is contained in place in the cylindrical containing part 34 provided at the distal end of the inner needle hub 12. Therefore, unlike the case where the hemostasis valve 76 and needle tip protector 78 are both contained in the containing part 54 of the outer needle hub 16, for example, the hemostasis valve 76 and needle tip protector 78 can be contained in place favorably and effectively within the assembly without increasing the entire length of the outer needle 14, and therefore, without increasing the size of the entire assembly.

Therefore, according to such indwelling needle assembly, blood leak through the outer needle 14 and inadvertent pricking accidents by the needle tip 18 of the inner needle 10 retracted from the outer needle 14 can be prevented in a highly effective way without causing difficulty in handling the larger size of the entire assembly or any impediment to the procedures of artificial dialysis or liquid and blood transfusions.

In the action ring 94 externally fitted about the protector main body 92 of the needle tip protector 78, the latching protrusion 152 that extends out into the containing part 54 of the outer needle hub 16 within the assembly of the inner needle hub 12 and outer needle hub 16 is integrally formed, and the integral movement of the action ring 94 and protector main body 92 is prevented, up to a given position of the protector main body 92, by the engagement of the latching protrusion 152 with the annular groove 70 of the containing part 54. Therefore, by means of making such latching protrusion 152 long enough, the length of the cylindrical containing part 34 of the inner needle hub 12 can be made favorably large. As a result, it becomes possible to make more room for the containing space of the protector main body 92 within the inner needle hub 12.

Furthermore, because of the circular reinforcing part 164 provided in the middle portion of its extending direction of the latching protrusion 152, the free length of the extended latching pieces 160 and 160 that extend out integrally from the end surface of the circular reinforcing part 164 in the axial direction can be made small, which reinforces the whole latching protrusion 152. Therefore, when the latching protrusion 152 is made long enough, reduction in latching force of the extended latching pieces 160 and 160 against the annular groove 70 of the containing part 54 can be effectively prevented. This makes it possible to arrange the containing space of the protector main body 92 within the inner needle hub 12 in a roomier size and maintain it for further advantages.

Also, the projected latching rim 162 is integrally formed along the outer periphery of the distal end of extended latching pieces 160 of the latching protrusion 152, which is latched to the outer needle hub 16 by having said projected latching rim 162 thrust into the annular groove 70 formed along the inner periphery of the containing part 54 of the outer needle hub 16. This gives an advantage that the latching of the latching protrusion 152 to the outer needle hub 16 is favorably carried out with a relatively simple structure. In addition, there is no need for relative positioning of the inner needle hub 12 and outer needle hub 16 in the circumferential direction in order to latch the latching protrusion 152 to the annular groove 70. That makes the assembly work of these inner needle hub 12 and outer needle hub 16 easier.

In the indwelling needle assembly of the present embodiment, the inner needle 10 slides along the inner periphery of the two (the first and second) insertion holes 108 and 110 made in the protector main body 92 of the needle tip protector 78 when the inner needle 10 provided with the needle tip protector 78 is retracted from the outer needle 14, but its part under the state of elastic deformation does not contact the outer periphery of the inner needle 10 with an urging force. Therefore, when the inner needle 10 is moved backward relative to the protector main body 92, no significant sliding resistance occurs based on the urging force between the inner periphery of the inner needle 10 and the protector main body 92.

Also, when the action ring 94 is located at a given advanced position of the protector main body 92 as a result of the advance movement of the action ring 94 following the retractive movement of such inner needle 10 relative to the protector main body 92, each of the flexible pieces 122 and 124 undergoes flexural and elastic deformation, and the needle tip 18 of the inner needle 10 can be covered and protected with each of the protection parts 130 and 131 of the protector main body 92.

And, the needle tip 18 of the inner needle 10 remains protected with each of the protection parts 130 and 131 during and after the process of retracting the inner needle 10 from the outer needle 14 or outer needle hub 16. Under such conditions, the action ring 94 stays put at the arranged position that places each of the protection parts 130 and 131 at a protective position, even if each of the flexible pieces 122 and 124 is inadvertently subject to flexural and elastic deformation toward the inner needle 10. For this reason, the conditions of protecting the needle tip 18 with each of the protection parts 130 and 131 can be securely maintained.

Therefore, by using the indwelling needle assembly of the present embodiment, protection of the needle tip 18 of the inner needle 10 can be carried out with the needle tip protector 78 with lesser force surely and immediately after removal of the inner needle 10 from the patient. In addition, the protected condition of the needle tip 18 of the inner needle 10 by the needle tip protector 78 can even be more securely maintained. As a result of it, an indwelling operation of the outer needle 14 in the patient can be carried out extremely safely and smoothly.

Also, the protector main body 92 is formed in a cylindrical shape having four side plates 100 to 106. For this reason, the distal end of the inner needle 10 including the needle tip 18 can be securely covered and protected with these four side plates 100 to 106.

Furthermore, among these four side plates 100 to 106, the first and second parallel side plates 104 and 106 are not only without any of the flexible pieces 122 and 124 but also provided with the first and second stopper plates 118 and 120, so that they are not easily subject to flexural and elastic deformation. Therefore, the protector main body 92 is in no way easily subject to deformation, even if the protector main body 92 containing the needle tip 18 inside is grasped by fingers after the retraction of the inner needle 10, as long as the first and second parallel side plates 104 and 106 are grasped. As a result, the effect of protecting the needle tip 18 of the inner needle 10 with the needle tip protector 78 can be further exerted.

At the distal end of such second parallel side plate 106 not easily subject to flexural and elastic deformation, the distal end-side bottom plate 98 is integrally formed, and a multitude of protruded engaging parts 142 protruding out in the direction orthogonal to the central axis P of the protector main body 92 are provided along the outer periphery of said distal end-side bottom plate 98. And, the advance movement of the action ring 94 relative to the protector main body 92 is restricted by the engagement with the multitude of engaging parts 142, while any slip-out from the distal end-side of the protector main body 92 is prevented. Therefore, a situation can be prevented favorably where the state of engagement between each protruded engaging part 142 and the action ring 94 becomes unstable due to changes in the direction of the multitude of protruded engaging parts 142 that engage with the action ring 94, even if, for example, the protector main body 92 containing the needle tip 18 inside is grasped by fingers after the retraction of the inner needle 10.

Also, since the second parallel side plate 106 is not subject to any deformation due to the advance movement of the action ring 94 relative to the protector main body 92, one can effectively avoid a situation where the distal end-side bottom plate 98 integrally formed with such second parallel side plate 106 and the protruded engaging part 142 provided therein are displaced inward or outward by the relative movement of the action ring 94 against the protector main body 92, or a situation where the protrusion angle of each protruded engaging part 142 relative to the central axis P of the protector main body 92, that is, the size of the angle between the central axis P and the surface where the protruded engaging part 142 comes in contact with the front end of the action ring 94 (shown as a in FIG. 8) is modified. This allows the protrusion angle a of each protruded engaging part 142 relative to the central axis P of the protector main body 92 to remain constant regardless, for example, of the flexural deformation or angle of each of the flexible pieces 122 and 124 of the first and second flexible side plates 100 and 102. As a result, the engagement of each protruded engaging part 142 with the front-end surface of the action ring 94 can be securely maintained, and the slip-out of the action ring 94 from the protector main body 92 can be surely prevented. Consequently, the conditions of protection of the needle tip 18 of the inner needle 10 with the protection parts 130 and 131 can be maintained even more securely.

Also, even when the needle tip 18 slips out of the second insertion hole 110 of the distal end-side bottom plate 98 due to an inadvertent retractive movement of the inner needle 10 from the state of protection of the needle tip 18 of the inner needle 10 with the protection parts 130 and 131, such needle tip 18 is housed within the proximal end-side closed space 140. Therefore, the needle tip 18 is prevented from protruding out of the protector main body 92 before it happens. This also allows the state of protection of the needle tip 18 of the inner needle 10 to be maintained even more securely after retraction of the inner needle 10 from the patient and others.

And, each of the flexible side plates 100 and 102 is made elastically deformable in addition to flexurally deformable. For that reason, unwanted flexural deformation of each of the flexible pieces 122 and 124 is prevented by the urging force exerted by the elasticity. Therefore, a situation can be effectively prevented where the two protection parts 130 and 131 get in touch with the outer periphery of the inner needle 10 to generate excess sliding resistance between the outer periphery of the inner needle 10 and the protector main body 92 due to unwanted flexural deformation of each of the flexible pieces 122 and 124 when the inner needle 10 is retracted from the patient.

By having the inner needle 10 inserted into the first and second insertion holes 108 and 110 made to position coaxially with the proximal end-side bottom plate 96 and distal end-side bottom plate 98 respectively that are arranged on the proximal end side and distal end side of the protector main body 92 apart from each other by a given distance, the needle tip protector 78 is mounted to the inner needle 10 in a slidable way. Therefore, when the inner needle 10 moves relative to the protector main body 92, the play of the inner needle 10 in the twisting direction can be restricted favorably to ensure a smoother movement of the inner needle 10 than in case of having it inserted into only one through-hole, for example.

The distal end-side bottom plate 98 where the second insertion hole 110 is made is provided on the second parallel side plate 106 integrally formed with the first parallel extension part 114 that is not subject to flexural deformation by the first and second stopper plates 118 and 120. For this reason, with respect to not only the proximal end-side bottom plate 96 where the first insertion hole 108 is formed but also the distal end-side bottom plate 98, the relative position and facing direction of these proximal end-side bottom plate 96 and the distal end-side bottom plate 98 do not change by flexural deformation of each of the flexible pieces 122 and 124 in association with movement of the action ring 94. Therefore, each position of the first insertion hole 108 and second insertion hole 110 remains the same, thereby stabilizing the state of external fit of the protector main body 92 about the inner needle 10, and even the movement of the protector main body 92 relative to the inner needle 10. As a result, while keeping the sliding resistance of the inner needle 10 to the inner periphery of the first and second insertion holes 108 and 110 at a minimum, the diameter of these first and second insertion holes 108 and 110 can be made small, and thus, the positioning accuracy of the protector main body 92 relative to the inner needle 10 is expected to be improved.

The first flexible piece 122 and second flexible piece 124 having the protection parts 130 and 131 respectively at their tips are each provided on the first flexible side plate 100 and second flexible side plate 102 that extend toward the distal end from the edge on both sides of, and sandwiching in between, the first insertion hole 108 of the proximal end-side bottom plate 96 located on the proximal end side of the protector main body 92. This allows the needle tip 18 of the inner needle 10 to be covered by the two protection parts 130 and 131 being sandwiched in between, due to flexural and elastic deformation of the two flexible pieces 122 and 124 following the advance movement of the action ring 94 relative to the protector main body 92. As a result, protection of the needle tip 18 of the inner needle 10 can be carried out more securely.

Each of the protection parts 130 and 131, bent in an L-shape, integrally possesses the first protection plates 132 and 133 as well as the second protection plates 134 and 135. This can favorably prevent detachment of the needle tip 18 of the inner needle 10 from the distal end-side closed space 138 housing thereof that is formed by each of the protection parts 130 and 131, even if the needle tip 18 of the inner needle 10 is displaced toward the first protection plates 132 and 133 or second protection plates 134 and 135 under the condition of being protected by each of the protection parts 130 and 131 because it comes in contact and is engaged with each of the protection plates 132 through 135.

At the protection parts 130 and 131 integrally formed with the first flexible piece 122, two lateral lid plates 136 and 136 that close each opening on both sides in the cross direction are provided. This allows the needle tip 18 of the inner needle 10 to be housed in the distal end-side closed space 138 under the state of being enclosed on all sides, thus enabling protection of the needle tip 18 of the inner needle 10 to be carried out more securely.

The arranged position of the action ring 94 is maintained relative to the protector main body 92 under the state of having the needle tip 18 of the inner needle 10 protected with the protection parts 130 and 131 by means of engagement of the anti-retraction tab 128 with the first and second engaging surfaces 148 and 150 provided on the action ring 94. This too allows the needle tip 18 of the inner needle 10 to be protected even more securely.

The first engaging surface 148 and second engaging surface 150 engaged with the anti-retraction tab 128 are configured with two side surfaces of the recessed groove 146 facing each other and formed on the end surface of the action ring 94. Because of this, the first engaging surface 148 and second engaging surface 150 can easily be provided all at once by simply forming the recessed groove 146 on the action ring 94. This will significantly contribute to simplification of the structure and improved manufacturability of the action ring 94 and even the needle tip protector 78.

The anti-retraction tab 128 is arranged, one each on both sides of the inner needle 10 sandwiched in between to be inserted into the two (the first and second) insertion holes 108 and 110, while the recessed groove 146 having the first and second engaging surfaces 148 and 150 is provided on the action ring 94 corresponding to each of the anti-retraction tabs 128. This allows the anti-retraction tab 128 to be engaged more securely with the first and second engaging surfaces 148 and 150. As a result, the effect of blocking the movement of the action ring 94 relative to the protector main body 92 at a given position can be exerted more definitely.

The anti-retraction tab 128 is provided one each on the first and second flexible side plates 100 and 102 that are to be flexurally and elastically deformed by the action ring 94 externally fitted about the protector main body 92. For this reason, the anti-retraction tab 128 is formed more easily than in case, for example, where pieces to be flexurally and elastically deformed by the action ring 94 are provided on the protector main body 92, aside from each of the flexible pieces 122 and 124, to form the anti-retraction tab 128. In addition, the anti-retraction tab 128 is integrally formed with each of the flexible pieces 122 and 124 by a cut-and-raise processing. This makes the formation of the anti-retraction tab 128 for each of the flexible pieces 122 and 124 even easier.

The protector main body 92 comprises a single unit made by flexurally deforming part of a metal plate in a given form. For this reason, manufacturability of the protector main body 92 and even the needle tip protector 78 as a whole can be effectively enhanced as compared to, for example, a case where various components are assembled and adhered to form the protector main body 92.

An embodiment of this invention has been explained above, which is just an example, and this invention is not to be interpreted in a limited sense because of specific descriptions of such embodiment.

It is also possible, for example, to form the latching protrusion 152 on the action ring 94 in a way extending out from one point, or three or more points, along the periphery thereof. Of course, the number of extended latching pieces can be varied as appropriate.

The latching structure of the latching protrusion against the outer needle hub is not limited to any given example, either. For example, in lieu of the latching groove, a stepped protrusion may be provided whereby a projected latching rim of a latching protrusion can be latched. It is also possible to adopt a structure wherein, while a protrusion is provided along the inner periphery of the containing part, a projected or depressed latching rim of a latching protrusion is provided to be latched against the protrusion of the containing part.

The protector main body 92 does not necessarily have to be contained in its entirety in the cylindrical containing part 34 of the inner needle hub 12, but part of the protector main body 92 may be arranged so as to extend out in the containing part 54 of the outer needle hub 16 via the distal end-side opening of the cylindrical containing part 34, as long as it does not increase each length of the inner needle hub 12 and outer needle hub 16 in the axial direction.

In the above embodiment, the protector main body 92 was formed using a single metal plate that is elastically deformable, but each of the flexible pieces 122 and 124, among components of the protector main body 92, does not necessarily require elasticity if provided with flexibility. On the other hand, the anti-retraction tab 128 must have elasticity. Therefore, the protector main body 92 can be formed with materials other than metals as long as it possesses characteristics required at each part. For example, the protector main body 92 can be formed in its entirety with resin materials, or configured by combining various materials with characteristics required at each part. In other words, it may be formed by assembling and adhering to each other some metal or resin components or components made of materials other than metal and resin.

Also, when resin materials are used as a formation material of the protector main body 92, in part or in whole, for example, polyolefin resins such as polyethylene, polypropylene, polybutadiene and ethylene-vinyl acetate copolymer, and polyester resins such as polyvinyl chloride, polyurethane, polystyrene, polymethylmethacrylate, polycarbonate, polyamide, polyethylene terephthalate, polybutylene terephthalate, and various resin materials such as acrylic resin, ionomer, polyacetal, polyphenylene sulfide, polyether ether ketone are used as formation materials either by itself or by combining two of more of these. Of course, as to the protector main body 92 formed by using these resin, the flexible side plate must have flexibility and the anti-retraction tab must have elasticity.

In the above embodiment, the anti-retraction tab 128 is formed on the first and second flexible side plates 100 and 102 where the first and second flexible pieces 122 and 124 are provided, but it can be formed on the first and second parallel side plates 104 and 106 where these flexible pieces 122 and 124 are not provided. In this case, the anti-retraction tab 128 can be formed, for example, by first providing a C-shaped slot that opens up toward the proximal end of the first and second parallel side plates 104 and 106, and then by a cut-and-raise processing whereby the proximal end of the part enclosed by this slot is bent to tilt outward from the protector main body 92. Also, the method of forming the slot is not limited to any particular one, but it can be formed easily by punching press work.

It is also possible to form the anti-retraction tab 128 by first making a simple C-shaped cut, instead of a slot, in the four side plates 100 to 106, and then by simply using this cut, or by a cut-and-raise processing whereby the part enclosed by the cut is bent outward from the protector main body 92.

The slots and cuts made in the four side plates 100 to 106 to form the anti-retraction tab 128 are not limited to C-shapes as shown in the example, but they can be in V-shapes, mound shapes or U-shapes.

It is also possible to provide an anti-retraction tab having a structure other than the cut-and-raise by means of, for example, integrally fixating an elongated small component as an anti-retraction tab at a given position of the protector main body 92 such as on the four side plates 100 to 106, or otherwise the proximal end-side bottom plate 96.

The first engaging surface 148 or second engaging surface 150 provided on the action ring 94 is not limited to any particular form, position or number of parts, as long as it engages with the anti-retraction tab 128 that is in contact with the rear-end surface of the action ring 94 to restrict elastic deformation of the anti-retraction tab 128 in the direction of getting closer to the inner needle 10.

Therefore, it is possible, for example, to form a recessed groove on the rear-end surface of the action ring continuously extending along the periphery thereof and form the first and second engaging surfaces using these two side surfaces of this recessed groove. It is also possible to provide depressions or recessed grooves in the number corresponding to the number of anti-retraction tabs on the rear-end surface of the action ring in contact with the anti-retraction tab, and form the first and second engaging surfaces on two inner surfaces each located on the inner and outer surface sides of the action ring, among the inner surfaces of these depressions or recessed grooves. In addition, one can provide a protrusion or a protruded strip extending along the periphery instead of the above depressions or recessed grooves, or in addition to them, on the rear-end surface of the action ring, and form the first and second engaging surfaces using the two side surfaces each located on the inner and outer surface sides of the action ring. Also, in forming the first engaging surface only, it is possible to form a step where the outer periphery of the action ring is made one step higher than the inner periphery and configure the first engaging surface using this step.

The form of the action ring is not limited to the rectangular frame as shown in the example, but it can be in any other forms as long as it is externally fittable about the protector main body. From that point of view, various forms can be adopted including, for example, a cylinder or an annular disc form, a C-shape form made by removing part of the circumference of such cylinder or annular disc form, or a polygonal frame form other than rectangles, as well as other forms made by removing part of the circumference of the forms of such rectangular or polygonal frames.

The number of the flexible pieces 122 and 124 or anti-retraction tabs 128 are not necessary two, but can be one each, as shown in FIG. 17. Or, it can be three or more. When a multitude of flexible pieces are provided, it is enough for at least one of them to have a protection part at its distal end.

The structure of the needle tip protector is not limited to the one shown in the example, either. It is good enough to comprise a protector main body and an action ring to be slipped thereon and to be configured wherein the flexible plate provided on the protector main body is flexurally deformed due to movement of the action ring relative to the protector main body so that the needle tip of the inner needle can be protected with a protection part formed at the distal end of the flexible plate.

Figure 19:
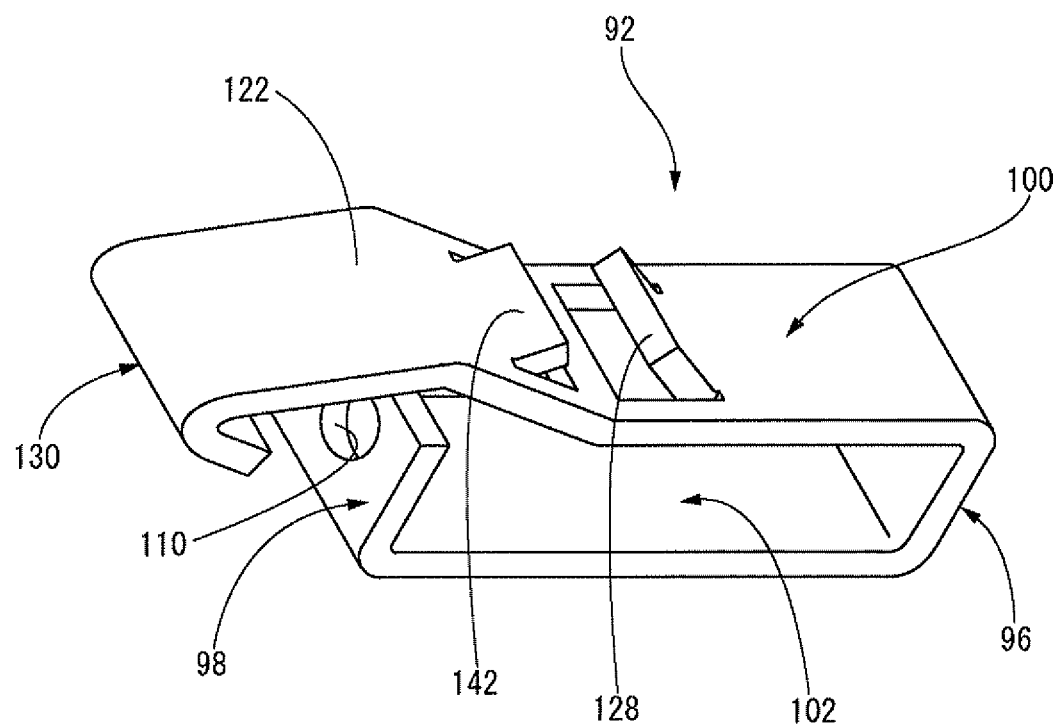
FIG. 19 is an explanatory axonometric view showing still another example of a needle tip protector related to this invention possessed by an indwelling needle assembly having a structure according to this invention.
Figure 20:
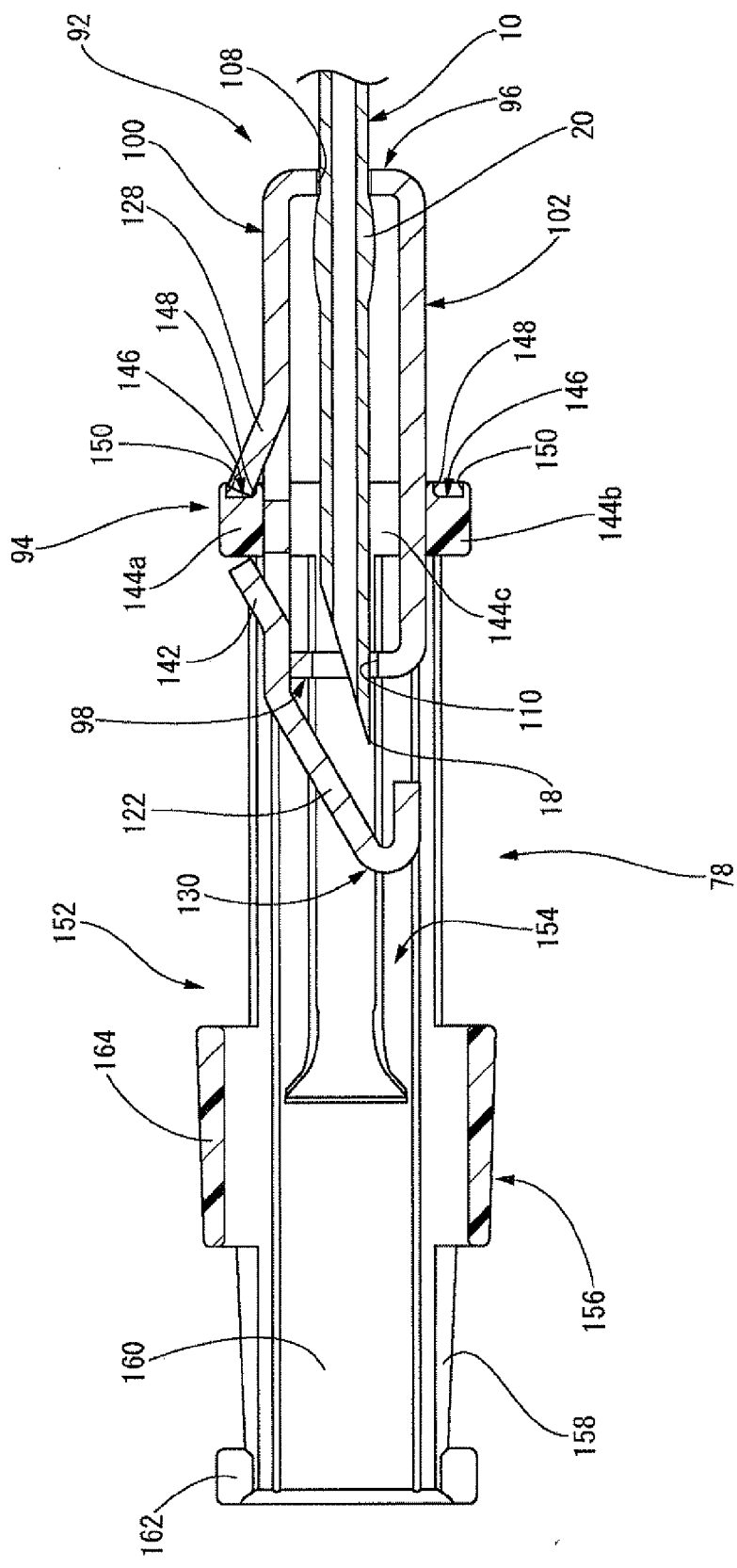
FIG. 20 is a diagram for explaining a usage of the needle tip protector shown in FIG. 19, which indicates a state where the needle tip of the inner needle is protected by a protection part through a relative movement of the protector main body against the action ring.

Therefore, as shown in FIG. 19, the protector main body 92 can also be configured by providing the first flexible piece 122, anti-retraction tab 128, protruded engaging part 142, and protection part 130 only on the first flexible side plate 100 omitting the first and second parallel side plates. In case of the needle tip protector 78 having such protector main body 92, the first flexible piece 122 is flexurally and elastically deformed by movement of the action ring 94 relative to the protector main body 92, as shown in FIG. 20, and when the needle tip 18 of the inner needle 10 becomes protected with the protection part 130, the anti-retraction tab 128 thrusts into the recessed groove 146 formed on the rear-end surface of the action ring 94. Also, under the same state, the action ring 94 is sandwiched between the anti-retraction tab 128 and protruded engaging part 142. This prevents unwanted movement of the action ring 94 and inadvertent flexural deformation of the first flexible piece 122 under the state of having the needle tip 18 of the inner needle 10 protected with the protection part 130, which securely maintains the state of protection of the needle tip 18 of the inner needle 10. As to the embodiment shown in FIGS. 19 and 20, a detailed explanation is omitted by using the same reference numerals as FIGS. 1 through 18 for the components and parts that have the same structure as those of the above first embodiment.

In addition, the structure of the hemostasis valve 76 contained in the containing part 54 of the outer needle hub 16 is not limited to any particular one shown in the example, either, and any conventionally known structure can be adopted.

Figure 21:
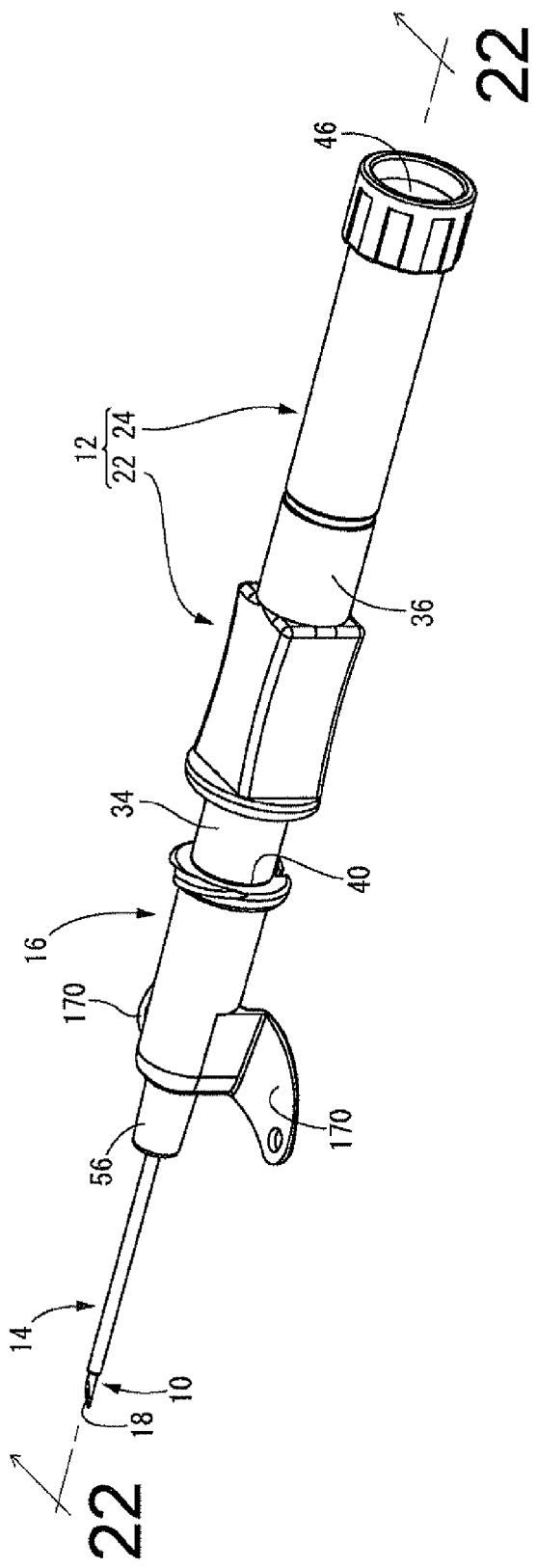
FIG. 21 is an explanatory axonometric view showing still another example of an indwelling needle assembly related to this invention provided with a needle tip protector having a structure according to this invention.
Figure 22:
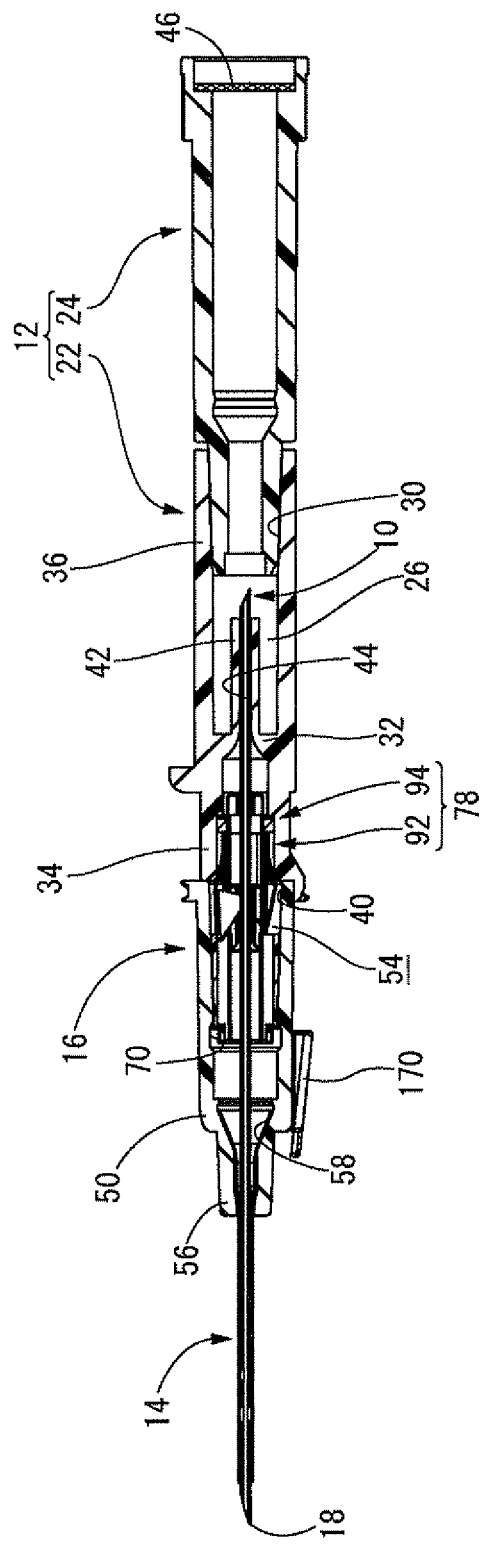
FIG. 22 is a section diagram taken along line 22-22 in FIG. 21.

Moreover, a wing-like part 170 may be provided that stretches out on both sides from the outer periphery of the outer needle hub 16, like the indwelling needle assembly shown in FIGS. 21 and 22, for example. Also, in the indwelling needle assembly of the present embodiment and the one described below, a similar needle tip protector to the one in the embodiments shown in FIGS. 1 through 18, or FIGS. 19 and 20 is provided.

Figure 23:
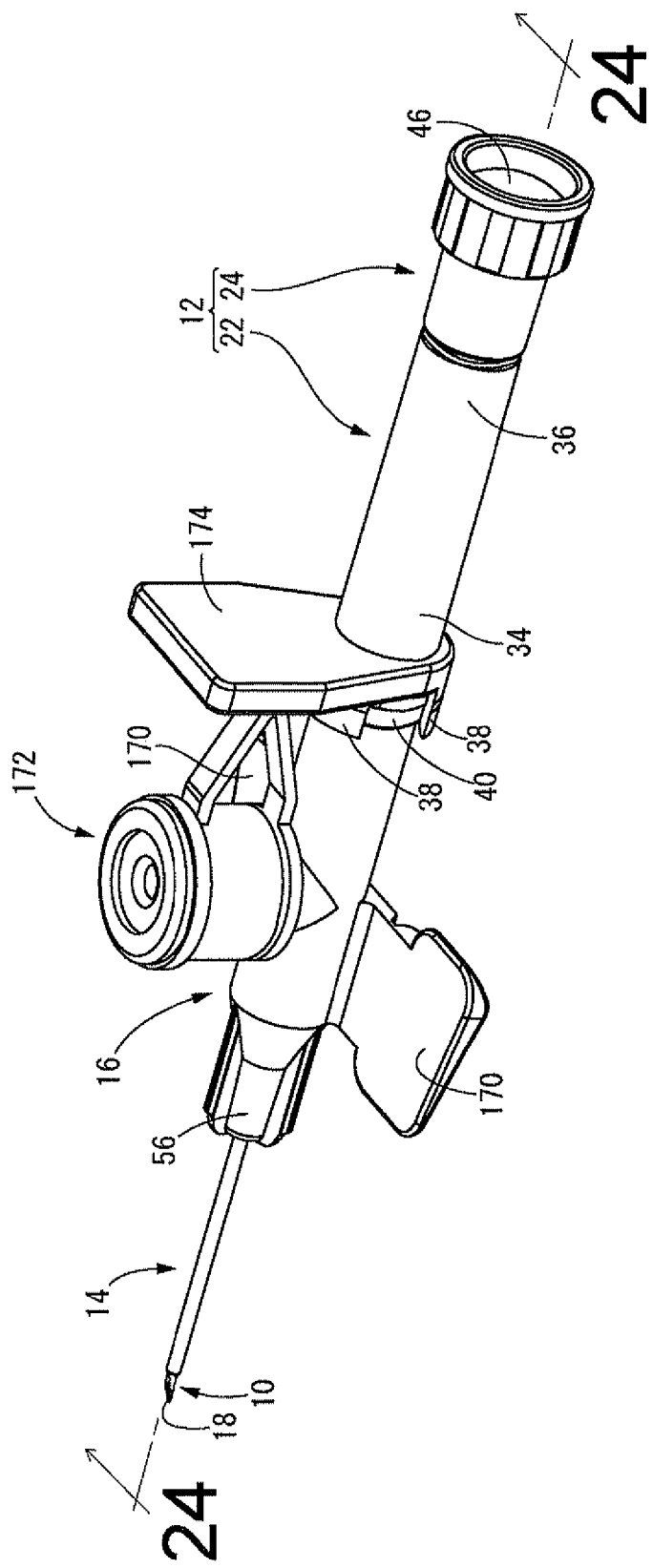
FIG. 23 is an explanatory axonometric view showing still another example of an indwelling needle assembly related to this invention provided with a needle tip protector having a structure according to this invention.
Figure 24:
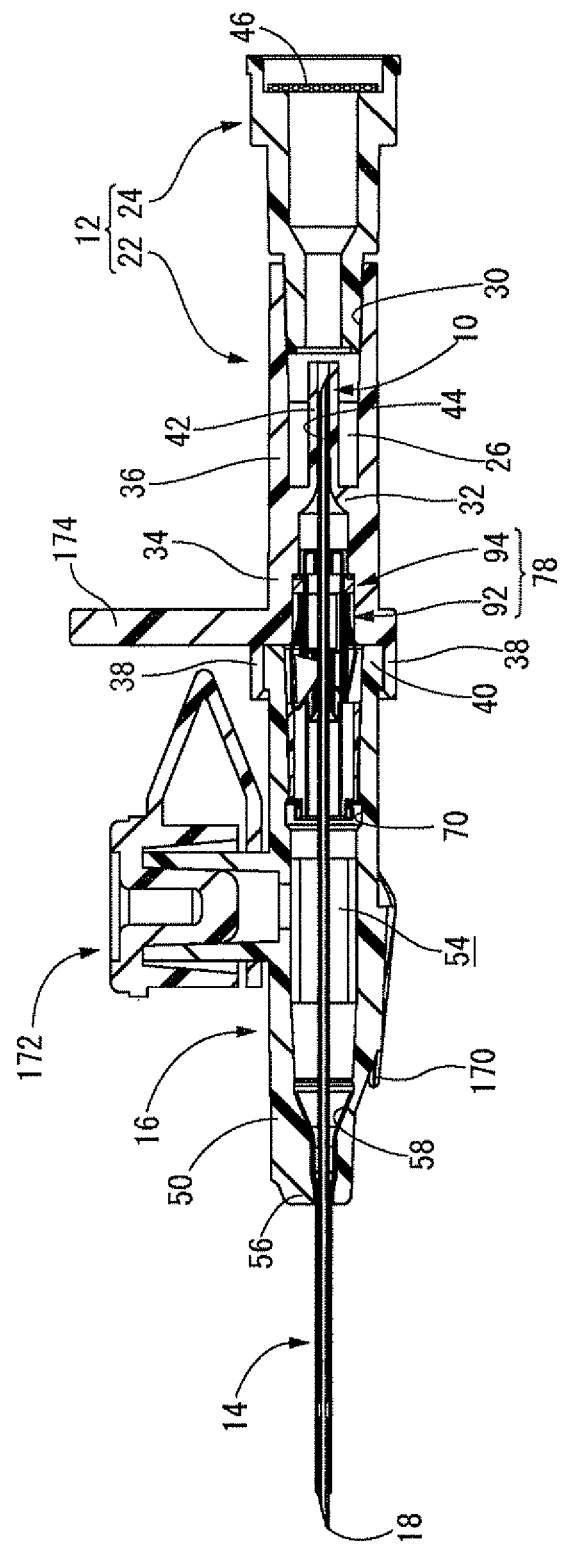
FIG. 24 is a section diagram taken along line 24-24 in FIG. 23.

Also, like the indwelling needle assembly shown in FIGS. 23 and 24, a mixed injection port 172 can be provided on the outer needle hub 16. Additionally, at the distal end of the inner needle hub 12, a protruded plate 174 is formed that protrudes out orthogonally to the needle axis direction, which can prevent the inner needle 10 from moving back relative to the outer needle 14 by gripping the protruded plate 174 with fingers in the insertion procedure.

| KEYS TO SYMBOLS | | | |
|---|---|---|---|
| 10 | Inner needle | 12 | Inner needle hub |
| 14 | Outer needle | 16 | Outer needle hub |
| 18 | Needle tip | 20 | Engaging part |
| 34 | Cylindrical containing part | 40 | Proximal end-side opening |
| 54 | Containing part | 70 | Annular groove |
| 76 | Hemostasis valve | 78 | Needle tip protector |
| 92 | Protector main body | 94 | Action ring |
| 96 | Proximal end-side bottom plate (Insertion passage formation wall) | | |
| 98 | Distal end-side bottom plate (Insertion passage formation wall) | | |
| 100 | First flexible side plate (flexible plate) | | |
| 102 | Second flexible side plate (flexible plate) | | |
| 104 | First parallel side plate | 106 | Second parallel side plate |
| 108 | First insertion hole (insertion passage) | | |
| 110 | Second insertion hole (insertion passage) | | |
| 112 | Bent part | 114 | First parallel extension part |
| 116 | Second parallel extension part | | |
| 118 | First stopper plate (stopper mechanism) | | |
| 120 | Second stopper plate (stopper mechanism) | | |
| 122 | First flexible piece | | |
| 124 | Second flexible piece | | |
| 128 | Anti-retraction tab (slip-out prevention mechanism) | | |
| 130 | Protection part | 131 | Protection part |
| 132, 133 | First protection plates | 134, 135 | Second protection plates |
| 136 | Lateral lid plate | 140 | Proximal end-side closed space (housing part) |
| 142 | Protruded engaging part (slip-out prevention mechanism) | | |
| 146 | Recessed groove | | |
| 148 | First engaging surface (slip-out prevention mechanism) | | |
| 150 | Second engaging surface | | |
| 152 | Latching protrusion | 160 | Extended latching piece |
| 162 | Projected latching rim | 164 | Circular reinforcing part |

The invention claimed is:

1. A needle tip protector comprising:

a protector main body having an insertion passage where a needle is inserted, the protector main body being mounted against the needle by means of having the needle inserted into the insertion passage such that the protector main body is movable in an axial direction of the needle while extending along the same direction;

at least one flexible plate attached to the protector main body and extending toward the needle tip at a location orthogonally away from the needle inserted into the insertion passage of the protector main body in a way that allows a distal end of the at least one flexible plate to undergo flexural deformation in a direction of getting closer to the needle;

a protection part placed at the distal end of the at least one flexible plate and that protects the needle tip by being placed at a protective position to cover the needle tip when the at least one flexible plate undergoes flexural deformation in the direction of having the distal end get closer to the needle in a state where the protector main body is moved toward the needle tip of the needle inserted into the insertion passage;

an action ring that is externally fitted about the protector main body in a movable way in the axial direction of the needle and allows the protection part to be placed in the protective position by causing flexural deformation of the distal end of the at least one flexible plate in the direction of having the distal end get closer to the needle through an advance movement toward a distal end side of the protector main body; and a slip-stop mechanism that prevents the action ring from slipping out of the protector main body in the axial direction of the needle, wherein the protector main body includes:

a proximal end-side bottom plate having a first insertion hole as the insertion passage and arranged on a proximal end side of the protector main body so as to extend and cross the axial direction of the needle, a pair of flexible side plates as the at least one flexible plate that are formed integrally with the proximal end-side bottom plate so as to extend from each of a pair of edges located on both sides of the first insertion hole of the proximal end-side bottom plate toward the needle tip of the needle inserted into the first insertion hole in a state of facing each other at a certain distance. the distance between opposing surfaces gradually increasing toward the needle tip to make the plates flexurally deformable in a direction of getting closer to each other, the protection part placed at the distal end of at least one of the pair of flexible side plates, a pair of parallel side plates facing each other in a direction orthogonal to the opposing direction of the at least one flexible side plate, the pair of parallel side plates extending parallel in the axial direction of the needle inserted into the first insertion hole, a distal end-side bottom plate having a second insertion hole as the insertion passage formed at a location closer to the needle tip of the needle than that of the first insertion hole and integrally formed with a proxiend edge of either of the pair of parallel side plates so as to extend toward each other at the distal end side of the protector main body, a housing part defined by a space enclosed by the distal end-side bottom plate, the proximal end-side bottom plate, the pair of flexible side plates and the pair of parallel side plates, and that houses a part of the needle inserted through the first insertion hole of the proximal end-side bottom plate and the second insertion hole of the distal end-side bottom plate, and a protruded engaging part integrally formed with the distal end-side bottom plate in a way that protrudes out of a surface of at least one of the pair of parallel side plates and the pair of flexible side plates, wherein as the action ring advances toward the distal end side of the protector main body, the protection part is placed at the protective position by having the pair of flexible side plates pushed inward with the action ring in the opposing direction of each other and flexurally deformed in the direction of getting closer to each other, and any slip-out of the action ring from the distal end side of the protector main body is prevented by means of engaging a front-end surface located on an advancing side of the action ring with the protruded engaging part of the distal end-side bottom plate.

2. The needle tip protector according to claim 1, wherein a bent part is provided at a midpoint in each extension direction of the pair of flexible side plates that bends a part closer to the distal end side than the midpoint in a direction away from the needle inserted in the first and second insertion holes, distal end sides of the bent part of the pair of flexible side plates are flexible pieces with the distance between the opposing surfaces gradually increasing toward the needle tip to make the plates flexurally deformable in the direction of getting closer to each other, proximal end sides of the bent part of the pair of flexible side plates are parallel extension parts that extend parallel to each other in the axial direction of the needle, and the pair of parallel extension parts are provided with a stopper mechanism that prevents flexural deformation in a direction of bringing the pair of flexible side plates closer to each other, and the pair of parallel side plates are integrally connected to the pair of parallel extension parts at each proximal end.

3. The needle tip protector according to claim 2, wherein a stopper plate is integrally formed with at least one of the pair of parallel extension parts extending toward at least another of the pair, and the stopper plate comprises the stopper mechanism and prevents the pair of parallel extension parts from flexurally deforming in the direction of getting closer to each other by means of having the stopper plate abut against the parallel extension part different from the one it is formed with.

4. The needle tip protector according to claim 1, wherein the distal end-side bottom plate is arranged so as to extend and cross orthogonally to the axial direction of the needle inserted into the first and second insertion holes, and the protruded engaging part extends from an edge of the distal end-side bottom plate in a direction orthogonal to the axial direction of the needle.

5. The needle tip protector according to claim 1, wherein the protection part is in a bent plate form having a first protection plate that extends from the distal end of the flexible plate toward the needle tip of the needle and a second protection plate that extends integrally from the distal end of the first protection plate closer to the needle tip in a direction opposite to the needle tip.

6. The needle tip protector according to claim 5, wherein the protection part is further provided with a pair of lateral lid plates facing each other in the direction orthogonal to the axial direction of the needle while placing the first and second protection plates of the protection part in between so as to cover each of lateral openings of the protection part in the bent plate form that open up to both sides in a direction orthogonal to the axial direction of the needle.

7. The needle tip protector according to claim 1, wherein the protector main body is a single unit that is made of a metal plate.

8. A needle tip protector comprising:

a protector main body having an insertion passage where a needle is inserted, the protector main body being mounted a against the needle b means of having the needle inserted into the insertion passage such that the protector main body is movable in an axial direction of the needle while extending along the same direction;

at least one flexible plate attached to the protector main body and extending toward the needle tip at a location orthogonally away from the needle inserted into the insertion passage of the protector main body in a way that allows a distal end of the at least one flexible plate to undergo flexural deformation in a direction of getting closer to the needle;

a protection part placed at the distal end of the at least one flexible plate and that protects the needle tip by being placed at a protective position to cover the needle tip when the at least one flexible plate undergoes flexural deformation in the direction of having the distal end get closer to the needle in a state where the protector main body is moved toward the needle tip of the needle inserted into the insertion passage;

an action ring that is externally fitted about the protector main body in a movable way in the axial direction of the needle and allows the protection part to be laced in the protective position by causing flexural deformation of the distal end of the at least one flexible plate in the direction of having the distal end get closer to the needle through an advance movement toward a distal end side of the protector main body; and a slip-stop mechanism that prevents the action ring from slipping out of the protector main body in the axial direction of the needle, wherein the slip-stop mechanism includes:

at least one anti-retraction tab provided on the protector main body in an elastically deformable way so as to extend toward the needle tip at a location orthogonally away from the axial direction of the needle inserted into the insertion passage of the protector main body, which allows the action ring to advance toward the distal end side of the protector main body by elastic deformation in the direction of getting closer to the needle, and when the protection part of the flexible plate is brought to the protective position by the action ring, the anti-retraction tab prevents the action ring from moving back toward a proximal end side of the protector main body by means of restoring from the state of elastic deformation and contacting a rear-end surface of the action ring located on an opposite side of an advancing direction of the action ring, and at least one first engaging surface placed on the rear-end surface of the action ring that restricts elastic deformation of the anti-retraction tab in the direction of getting closer to the needle by engaging itself with the anti-retraction tab in contact with the rear-end surface, wherein an insertion passage formation wall that forms the insertion passage is provided on the proximal end side of the protector main body so as to extend and cross the axial direction of the needle inserted into the insertion passage, the at least one flexible plate comprises two flexible plates that are integrally formed with the insertion passage formation wall so as to extend toward the needle tip in a state of facing each other placing the needle inserted into the insertion passage in between, and the distance between opposing surfaces of the two flexible plates is increased toward the needle tip, and as the action ring advances toward the needle tip, the two flexible plates are pressed in the direction of getting closer to the needle along an inner periphery of the action ring, thereby being flexurally deformed in the direction of getting closer to each other.

9. The A needle tip protector comprising:

a protector main body having an insertion passage where a needle is inserted, the protector main body being mounted against the needle by means of having the needle inserted into the insertion passage such that the protector main body is movable in an axial direction of the needle while extending along the same direction;

at least one flexible plate attached to the protector main body and extending toward the needle tip at a location orthogonally away from the needle inserted into the insertion passage of the protector main body in a way that allows a distal end of the at least one flexible plate to undergo flexural deformation in a direction of getting closer to the needle;

a protection part placed at the distal end of the at least one flexible plate and that protects the needle tip by being placed at a protective position to cover the needle tip when the at least one flexible plate undergoes flexural deformation in the direction of having the distal end get closer to the needle in a state where the protector main body is moved toward the needle tip of the needle inserted into the insertion passage:

an action ring that is externally fitted about the protector main body in a movable way in the axial direction of the needle and allows the protection part to be placed in the protective position by causing flexural deformation of the distal end of the at least one flexible plate in the direction of having the distal end get closer to the needle through an advance movement toward a distal end side of the protector main body; and a slip-stop mechanism that prevents the action ring from slipping out of the protector main body in the axial direction of the needle;

wherein the slip-stop mechanism includes:

at least one anti-retraction tab provided on the protector main body in an elastically deformable way so as to extend toward the needle tip at a location orthogonally away from the axial direction of the needle inserted into the insertion passage of the protector main body, which allows the action ring to advance toward the distal end side of the protector main body by elastic deformation in the direction of getting closer to the needle, and when the protection part of the flexible plate is brought to the protective position by the action ring, the anti-retraction tab prevents the action ring from moving back toward a proximal end side of the protector main body by means of restoring from the state of elastic deformation and contacting a rear-end surface of the action ring located on an opposite side of an advancing direction of the action ring, and at least one first engaging surface placed on the rear-end surface of the action ring that restricts elastic deformation of the anti-retraction tab in the direction of getting closer to the needle by engaging itself with the anti-retraction tab in contact with the rear-end surface, wherein the at least one anti-retraction tab comprises two anti-retraction tabs that are provided on the protector main body so as to extend toward the needle tip in a state of being placed on both sides of the needle, and at least one first engaging surface comprises two first engaging surfaces that are each provided on the rear-end surface of the action ring being in contact with the two anti-retraction tabs.

10. The needle tip protector according to claim 9, wherein a second engaging surface is further provided on the rear-end surface of the action ring so as to restrict elastic deformation of the anti-retraction tab in the direction away from the needle by engaging itself with the anti-retraction tab in contact with the rear-end surface.

11. The needle tip protector according to claim 10, wherein a recessed groove is provided on the rear-surface of the action ring extending along a periphery of the action ring, and the first and second engaging surfaces are each configured on two side surfaces that extend along a periphery of the recessed groove.

12. An indwelling needle assembly comprising:

an inner needle hub;

an inner needle that extends out from a distal end of the inner needle hub;

a hollow outer needle hub;

a hollow outer needle that extends out from a distal end of the outer needle hub, the inner and outer needle hubs being assembled with each other by having the distal end of the inner needle hub inserted into a proximal end-side opening of the outer needle hub under a state where the inner needle is inserted into the outer needle;

a needle tip protector including:

a protector main body having an insertion passage where a needle is inserted, the protector main body being mounted against the needle by means of having the needle inserted into the insertion passage such that the protector main body is movable in an axial direction of the needle while extending along the same direction;

at least one flexible plate attached to the protector main body and extending toward the needle tip at a location orthogonally away from the needle inserted into the insertion passage of the protector main body in a way that allows a distal end of the at least one flexible pate to undergo flexural deformation in a direction of getting closer to the needle;

a protection part placed at the distal end of the at least one flexible plate and that protects the needle by being placed at a protective position to cover the needle tip when the at least one flexible plate undergoes flexural deformation in the direction of having the distal end get closer to the needle in a state where the protector main body is moved toward the needle tip of the needle inserted into the insertion passage;

an action ring that is externally fitted about the protector main body in a movable way in the axial direction of the needle and allows the protection part to be placed in the protective position by causing flexural deformation of the distal end of the at least one flexible plate in the direction of having the distal end get closer to the needle through an advance movement toward a distal end side of the protector main body; and a slip-stop mechanism that prevents the action ring from slipping out of the protector main body in the axial direction of the needle, the needle tip protector being mounted to the inner needle;

a hemostasis valve arranged to fit in a distal end side of the outer needle hub so as to prevent a blood flow into the outer needle hub from flowing out of the proximal end-side opening through an inner hole of the outer needle in a state where the inner needle is retracted from the outer needle;

a cylindrical containing part that extends in an axial direction of the inner needle being provided on a distal end side of the inner needle hub at a distance from an outer periphery of the inner needle, the protector main body mounted to the inner needle and the action ring being externally fitted about the protector main body such that the protector main body and the action ring are arranged to fit in the cylindrical containing part; and a latching protrusion integrally formed with the action ring that extends out into the outer needle hub via a distal end-side opening of the cylindrical containing part, wherein the action ring is advanced relative to the protector main body as the inner needle and the protector main body move integrally when the inner needle is retracted from within the outer needle by having the latching protrusion latched to the outer needle hub, and the protection part is placed at the protective position by flexurally deforming the flexible plate.

13. The indwelling needle assembly according to claim 12, wherein the latching protrusion of the action ring includes a circular reinforcing part that is provided in a middle portion of its extending direction and does not interfere with the protector main body and multiple extended latching pieces that are latched to the outer needle hub extending out from the circular reinforcing part into the outer needle hub.

14. The indwelling needle assembly according to claim 12, wherein an annular groove is formed along an inner peripheral surface of the outer needle hub extending continuously in its circumferential direction, and a projected latching rim that is formed protruding from a distal end of the latching protrusion thrusts into the annular groove to be latched.

15. The indwelling needle assembly according to claim 12, wherein a protruded engaging part that releases an engagement of the latching protrusion with the outer needle hub is provided on the protector main body by means of engaging itself with the action ring and moving the action ring integrally with the protector main body when the inner needle and the protector main body move integrally further from a state where the protection part is placed at the protective position due to the flexural deformation of the flexible plate.

* * * * *